United States Patent
Yasuda et al.

(10) Patent No.: US 7,238,720 B2
(45) Date of Patent: Jul. 3, 2007

(54) PHARMACEUTICAL USE OF N-CARBAMOYLAZOLE DERIVATIVES

(75) Inventors: Nobuyuki Yasuda, Tsuchiura (JP); Tadashi Nagakura, Ushiku (JP); Kazuto Yamazaki, Tsukuba (JP); Seiji Yoshikawa, Tsukuba (JP); Toshimi Okada, Tsuchiura (JP); Hironori Ikuta, Ushiku (JP); Mika Koyanagi, Tsukuba (JP)

(73) Assignee: Eisai R & D Management Co. Ltd., Tokyo (JP)

( * ) Notice: Subject to any disclaimer, the term of this patent is extended or adjusted under 35 U.S.C. 154(b) by 443 days.

(21) Appl. No.: 10/766,388

(22) Filed: Jan. 27, 2004

(65) Prior Publication Data

US 2004/0186153 A1  Sep. 23, 2004

Related U.S. Application Data

(62) Division of application No. 10/147,105, filed on May 15, 2002, now abandoned.

(30) Foreign Application Priority Data

May 18, 2001 (JP) .............................. 2001-149983

(51) Int. Cl.
  *A61K 31/4196*  (2006.01)
  *A61K 31/416*  (2006.01)
  *C07D 43/02*  (2006.01)

(52) U.S. Cl. .................... 514/383; 514/406; 548/263.2; 548/265.4

(58) Field of Classification Search ................ 514/383; 548/263.2
See application file for complete search history.

(56) References Cited

U.S. PATENT DOCUMENTS 5,510,320 A * 4/1996 Tseng .......................... 504/273
6,492,301 B1 * 12/2002 Hacker et al. .............. 504/128

* cited by examiner

*Primary Examiner*—Kamal A. Saeed
(74) *Attorney, Agent, or Firm*—Morgan & Finnegan, LLP

(57) ABSTRACT

The present invention relates to use of 1-carbamoylazole derivatives as medicaments and pharmaceutical compositions containing 1-carbamoylazole derivatives as the active ingredient, based on their DPPIV inhibiting effects. The present invention provides a dipeptidyl peptidase IV inhibiting agent comprising a compound represented by the general formula (I):

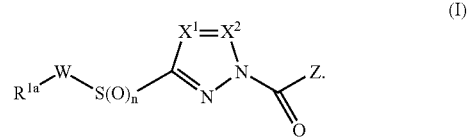

3 Claims, No Drawings

PHARMACEUTICAL USE OF N-CARBAMOYLAZOLE DERIVATIVES

This Application is a Divisional of U.S. application Ser. No. 10/147,105 filed on 15 May 2002, now abandoned, which in turn claims foreign priority under 35 U.S.C. 119 to applications filed in Japan, serial number 2001-149983, filed 18 May 2001.

FIELD OF THE INVENTION

The present invention relates to use of 1-carbamoylazole derivatives as medicaments and pharmaceutical compositions containing 1-carbamoylazole derivatives as the active ingredient, based on their DPPIV inhibiting effects.

BACKGROUND OF THE INVENTION

Dipeptidyl peptidase IV (DPPIV) is a serine protease which specifically hydrolyzes dipeptide X-Pro from the free N-terminus of polypeptide chains.

Glucose-dependent insulin-release stimulating hormones secreted from the intestinal tract after meals, that is, incretins (GLP-1, glucagon-like peptide-1, and GIP, glucose-dependent insulinotropic polypeptide) are degraded and inactivated rapidly by DPPIV. It is shown that the suppression of this degradation due to DPPIV enhances the action by incretins (GLP-1 and GIP) and increases insulin secretion from pancreas β-cells resulting from glucose stimulation, resulting in improvement in high levels of blood glucose after oral glucose tolerance tests (Diabetologia, 1999, November 42(11):1324–31). It is also shown that GLP-1 is involved in effects of suppressing appetite and amounts of eating, and has protecting action of the β-cells based on promoting the differentiation and proliferation of pancreas β-cells.

Thus, it is likely expected that DPPIV inhibitors can be useful agents for the treatment and prophylaxis of diseases, such as obesity and diabetes, in which GLP-1 and GIP are involved.

In addition, many publications report the relationship between various diseases and dipeptidyl peptidase IV as described below, and therefore it is also likely expected that DPPIV inhibition can provide agents for their treatment:

(1) agents for the prophylaxis and treatment of AIDS (Science, 262, 2045–2050, 1993);

(2) agents for the prophylaxis and treatment of osteoporosis (Clinical Chemistry, 34, 2499–2501, 1988);

(3) agents for the prophylaxis and treatment of intestinal disorders (Endocrinology, 141, 4013–4020, 2000);

(4) agents for the prophylaxis and treatment of diabetes, obesity, and hyperlipemia (Diabetes, 47, 1663–1670, 1998; Life Sci., 66(2), 91–103, 2000);

(5) agents for the prophylaxis and treatment of neovascularization (Agents and Actions, 32, 125–127, 1991);

(6) agents for the prophylaxis and treatment of infertility (WO 00/56296);

(7) agents for the prophylaxis and treatment of inflammatory disorders, autoimmune disease, and rheumatoid arthritis (J. Immunology, 166, 2041–2048, 2001); and (8) agents for the prophylaxis and treatment of cancers (Br J. Cancer, 1999, March, 79(7–8), 1042–8; J. Androl., March–April., 21(2), 220–6(2000)).

1-Carbamoylazole derivatives are known to be useful as herbicides, as described in U.S. Pat. Nos. 3,308,131, 5,258,361, 5,338,720, 5,424,279 and 5,510,320; and Japanese Patent Application Laid-open (JP-A) Nos. 5-255318, 9-143181 and 11-80137, but there is no report on DPPIV inhibiting effects.

DDPIV inhibitors are disclosed in, for example, U.S. Pat. Nos. 5,543,396, 6,011,155 and 6,303,661; US-A1-20010020006; and WO 00/34241. However, they are distinctly different in structure from those of the present invention.

SUMMARY OF THE INVENTION

As described above, it is highly desired to provide DPPIV inhibiting compounds that are useful as medicaments. However, compounds have not yet been found which can provide a superior DPPIV inhibiting effect and can act effectively in clinical situations with great utility as medicaments. Therefore, an object of the present invention is to provide DPPIV inhibiting compounds that are useful as agents for the treatment, prophylaxis and improvement of diabetic diseases and the like.

The inventors have carried out intensive researches in view of the above-described circumstances, and found that N-carbamoylazole derivatives possess a DPPIV inhibiting effect.

The DPPIV inhibitors according to the present invention are useful as agents for treatment and prophylaxis, for example, such as diabetes treating agents, obesity treating agents, hyperlipemia treating agents, AIDS treating agents, osteoporosis treating agents, intestinal disorder treating agents, neovascularization treating agents, infertility treating agents, anti-inflammatory agents, anti-allergic agents, immune-modulating agents, hormone-modulating agents, antirheumatic agents, and cancer treating agents.

The inventors have conducted tests employing a glucose-tolerance effect as an indicator, in order to confirm the efficacy of these compounds through oral administration, and confirmed an oral effectiveness and found utilities as medicaments.

That is, the present inventors have found following inventions <1> to <9>:

<1> A dipeptidyl peptidase IV inhibiting agent comprising a compound represented by following general formula (I):

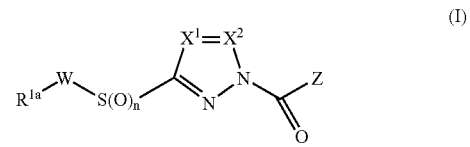

wherein $R^{1a}$ represents a $C_{1-6}$ alkyl group, a $C_{3-8}$ cycloalkyl group, a 5- to 10-menbered aromatic heterocyclic group, a $C_{6-10}$ aromatic hydrocarbon-cyclic group, a 4- to 10-menbered heterocyclic group, or a $C_{4-13}$ polycycloalkyl group;

n means an integer of 0 to 2;

W represents a single bond, a $C_{1-6}$ alkylene group, or a group represented by following formula W-1:

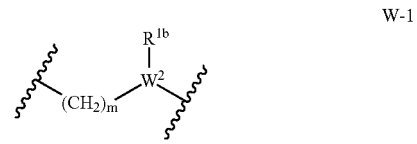

wherein $W^2$ represents a nitrogen atom or methine group, m means an integer of 0 to 3, and $R^{1b}$ represents a $C_{1-6}$ alkyl group, a $C_{3-8}$ cycloalkyl group, a 5- to 10-menbered aromatic heterocyclic group, a $C_{6-10}$ aromatic hydrocarbon-cyclic group, a 4- to 10-menbered heterocyclic group, or a $C_{4-13}$ polycycloalkyl group;

each of $X^1$ and $X^2$ independently represents a nitrogen atom or a methine group;

Z represents a group represented by following formula Z-1 or Z-2:

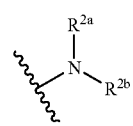

Z-1

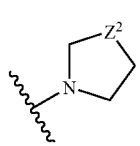

Z-2 wherein each of $R^{2a}$ and $R^{2b}$ independently represents a $C_{1-6}$ alkyl group, a $C_{2-6}$ alkenyl group, or a phenyl group, and $Z^2$ represents a sulfur atom or a methylene group; and wherein $R^{1a}$ and $R^{1b}$ may be substituted with one to three substituents selected from the group consisting of (1) halogen atoms, (2) a hydroxyl group, (3) $C_{2-6}$ alkenyl groups, (4) $C_{2-6}$ alkynyl groups, (5) a phenyl group, (6) a cyano group, (7) $C_{1-6}$ alkoxy groups which may be substituted with one to three halogen atoms or $C_{1-6}$ alkoxy groups, and (8) $C_{1-6}$ alkyl groups which may be substituted with one to three halogen atoms or $C_{1-6}$ alkoxy groups.

<2> The dipeptidyl peptidase IV inhibiting agent according to above-described item <1>, wherein Z is a group represented by following formula Z-3:

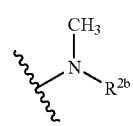

Z-3 wherein $R^{2b}$ represents a $C_{1-6}$ alkyl group, a $C_{2-6}$ alkenyl group, or a phenyl group.

<3> The dipeptidyl peptidase IV inhibiting agent according to above-described item <1> or <2>, wherein $R^{1a}$ is a phenyl group or a 4-pyrazolyl group.

<4> The dipeptidyl peptidase IV inhibiting agent according to any one of above-described items <1> to <3>, wherein $X^1$ is a nitrogen atom, and $X^2$ is a methine group.

<5> The dipeptidyl peptidase IV inhibiting agent according to any one of above-described items <1> to <3>, wherein $X^1$ and $X^2$ are methine group.

<6> The dipeptidyl peptidase IV inhibiting agent according to any one of above-described items <1> to <5>, wherein n is 1 or 2.

<7> The dipeptidyl peptidase IV inhibiting agent according to any one of above-described items <1> to <6>, wherein the inhibiting agent is an agent for the treatment and prophylaxis of diabetic diseases.

<8> The dipeptidyl peptidase IV inhibiting agent according to any one of above-described items <1> to <6>, wherein the inhibiting agent is an agent for the treatment and prophylaxis of obesity.

<9> The dipeptidyl peptidase IV inhibiting agent according to any one of above-described items <1> to <6>, wherein the inhibiting agent is a hyperlipemia treating agent, an AIDS treating agent, an osteoporosis treating agent, an agent for treating intestinal disorders, a neovascularization treating agent, an infertility treating agent, an anti-inflammatory agent, an anti-allergic agent, an immune-modulating agent, a hormone-modulating agent, an antirheumatic agent, or an agent for treating cancers.

DETAILED DESCRIPTION OF THE PREFERRED EMBODIMENT

The following explains the meaning of terms, symbols, and other used in the present specification and the present invention will be described in detail.

In the present specification, the structure formula of a compound gives a specific isomer for the sake of convenience in some cases, but the present invention includes isomers, such as all geometrical isomers derived from the structure of a compound, optical isomers, stereoisomers and tautomers, and mixtures of isomers on the basis of an asymmetrical carbon, which are not limited to the description of the formula indicated for convenience sake, and can be any one of the isomers or a mixture thereof. Therefore, although an asymmetrical carbon atom or atoms can be present in the molecule, thereby allowing an optically active substance or racemic form to exist, these are not limited specifically and both are included in the present invention. Furthermore, although polymorphic forms of crystals may exist, these are not limited as well, and the present invention can include one of such crystal forms or a mixture thereof. In addition, even if a compound of the present invention may be an anhydride or hydrate, the present invention may include such an anhydride and hydrate.

As used herein, "$C_{1-6}$ alkyl group" refers to a linear or branched alkyl group having one to six carbon atoms. Examples of "$C_{1-6}$ alkyl group" may include methyl, ethyl, n-propyl, i-propyl, n-butyl, i-butyl, t-butyl, n-pentyl, i-pentyl, neopentyl, n-hexyl, 1-methylpropyl, 1,2-dimethylpropyl, 2-ethylpropyl, 1-methyl-2-ethylpropyl, 1-ethyl-2-methylpropyl, 1,1,2-trimethylpropyl, 1-methylbutyl, 2-methylbutyl, 1,1-dimethylbutyl, 2,2-dimethylbutyl, 2-ethylbutyl, 1,3-dimethylbutyl, 2-methylpentyl, 3-methylpenthyl groups and the like.

As used herein, "$C_{2-6}$ alkenyl group" refers to a linear or branched alkenyl group having two to six carbon atoms. Examples of "$C_{2-6}$ alkenyl group" may include, for example, vinyl, allyl, 1-propenyl, isopropenyl, 1-buten-1-yl, 1-buten-2-yl, 1-buten-3-yl, 2-buten-1-yl, 2-buten-2-yl groups and the like.

As used herein, "$C_{2-6}$ alkynyl group" refers to a linear or branched alkynyl group having two to six carbon atoms. Examples of "$C_{2-6}$ alkynyl group" may include, for example, ethynyl, 1-propynyl, 2-propynyl, butynyl, pentynyl, hexynyl groups and the like.

As used herein, "$C_{3-8}$ cycloalkyl group" refers to a cyclic aliphatic hydrocarbon group having three to eight carbon atoms. Examples of "$C_{3-8}$ cycloalkyl group" may include, for example, cyclopropyl, cyclobutyl, cyclopentyl, cyclohexyl, cycloheptyl, cyclopropenyl, cyclobutenyl, cyclopentenyl, cyclohexenyl, cycloheptenyl groups and the like.

As used herein, "$C_{1-6}$ alkylene group" refers to a divalent group which is derived from the above-defined "$C_{1-6}$ alkyl group" by removing an additional hydrogen atom. Examples of "$C_{1-6}$ alkyl group" may include, for example, methylene, 1,2-ethylene, 1,3-propylene groups, and preferably a methylene group.

As used herein, "halogen atom" refers to a fluorine atom, a chlorine atom, a bromine atom, and an iodine atom. A fluorine atom and a chlorine atom are preferable.

As used herein, "$C_{1-6}$ alkoxy group" refers to a oxy group attached to above-defined "$C_{1-6}$ alkyl group". Examples of "$C_{1-6}$ alkoxy group" may include methoxy, ethoxy, n-propoxy, i-propoxy, sec-propoxy, n-butoxy, i-butoxy, sec-butoxy, t-butoxy, n-pentyloxy, i-pentyloxy, sec-pentyloxy, n-hexoxy, i-hexoxy, 1,1-dimethylpropoxy, 1,2-dimethylpropoxy, 2,2-dimethylpropoxy, 2-ethylpropoxy, 1-methyl-2-ethylpropoxy, 1-ethyl-2-methylpropoxy, 1,1,2-trimethylpropoxy, 1,1-dimethylbutoxy, 1,2-dimethylbutoxy, 2,2-dimethylbutoxy, 2,3-dimethylbutoxy, 1,3-dimethylbutoxy, 2-ethylbutoxy, 2-methylpentoxy, 3-methylpenthoxy, hexyloxy groups and the like.

As used herein, "$C_{6-10}$ aromatic hydrocarbon-cyclic group" refers to a hydrocarbon-cyclic group which is aromatic and has six to ten carbon atoms. Examples of "$C_{6-10}$ aromatic hydrocarbon-cyclic group" may include phenyl, 1-naphthyl, 2-naphthyl groups, and preferably a phenyl group.

As used herein, "heteroatom" refers to a sulfur atom, an oxygen atom, or a nitrogen atom.

As used herein, "5- to 10-membered aromatic heterocyclic group" refers to an aromatic cyclic group in which the ring of the cyclic group is composed of five to ten atoms and one or more heteroatoms are contained in the atoms constituting the ring of the cyclic group. "5- to 10-membered aromatic heterocyclic rings" of the "5- to 10-membered aromatic heterocyclic group" include in particular, for example, pyridine, thiophene, furan, pyrrole, oxazole, isoxazole, thiazole, isothiazole, imidazole, triazole, pyrazole, furazan, thiadiazole, oxadiazole, pyridazine, pyrimidine, pyrazine, indole, isoindole, indazole, chromene, quinoline, isoquinoline, cinnoline, quinazoline, quinoxaline, naphthyridine, phthalazine, purine, pteridine, thienofuran, imidazothiazole, benzofuran, benzothiophene, benzoxazole, benzothiazole, benzothiadiazole, benzimidazole, imidazo[1,2-a]pyridine, pyrrolopyridine, pyrrolopyrimidine, pyridopyrimidine rings and the like, and preferably pyridine, thiophene, furan, pyrrole, oxazole, isoxazole, thiazole, isothiazole, imidazole, triazole, pyrazole, thiadiazole, oxadiazole, pyridazine, pyrimidine, pyrazine rings and the like, and more preferably pyridine, isoxazole, thiazole, isothiazole, imidazole, triazole, pyrazole, pyridazine, pyrimidine, pyrazine rings and the like, and further preferably pyridine, imidazole, triazole, pyrazole, pyridazine, pyrimidine, pyrazine rings and the like.

"$C_{4-13}$ polycyclic aliphatic hydrocarbon" refers to an aliphatic hydrocarbon consisting of two or more rings and having four to thirteen carbon atoms. Specific examples may include, for example, bicyclo[1.1.0]butane, spiro[2.2]pentane, bicyclo[2.1.0]pentane, bicyclo[3.1.0]hexane, bicyclo[4.1.0]heptane, norbornane, nortricyclane, quadricyclane, bicyclo[3.3.0]octane, bicyclo[2.2.2]octane, bicyclo[4.3.0]nonane, bicyclo[3.3.1]nonane, bicyclo[4.4.0]decane, spiro[5,4]decane, perhydroquinacene, adamantane, bicyclo[3.3.3]undecane, perhydroanthracene, and the like.

As used herein, "$C_{4-13}$ polycycloalkyl group" refers to a cyclic aliphatic hydrocarbon group consisting of two or more rings and having four to thirteen carbon atoms, and specifically represents a monovalent group which is derived from the above-described "$C_{4-13}$ polycyclic aliphatic hydrocarbon" by removing one hydrogen atom at a given position, and in particular, endo-norbornane-2-yl group, 1-adamantyl group and the like.

As used herein, "4- to 10-membered heterocyclic group" refers to an cyclic group in which the ring of the cyclic group is composed of four to ten atoms and one or more heteroatoms are contained in the atoms constituting the ring of the cyclic group, with the exception of those included in the above-described "5- to 10-membered aromatic heterocyclic groups." "4- to 10-membered heterocyclic rings" of the "4- to 10-membered heterocyclic group" include, for example, aziridine, azetidine, oxetane, pyrrolidine, piperidine, tetrahydrofuran, tetrahydropyran, morpholine, thiomorpholine, piperazine, thiazolidine, azepine, dioxane, dioxolane, imidazoline, thiazoline, tetrahydroquinoline, tetrahydroisoquinoline, dihydrobenzopyran, dihydrobenzofuran, chroman, dihydroindole, 8-azabicyclo[3.2.1]octane and the like.

In the general formula (I) of the compounds of the present invention, n means an integer of 0 to 2, and preferably 1 or 2, and more preferably 2.

In the general formula (I) of the compounds of the present invention, m means an integer of 0 to 3, and preferably 0 or 1, and more preferably 0.

In general formula (I) of the compounds of the present invention, W represents a single bond, a $C_{1-6}$ alkylene group, or a group represented by the above-described formula W-1, wherein $W^2$ represents a nitrogen atom or a methine group, m means an integer of 0 to 3, and $R^{1b}$ represents a $C_{1-6}$ alkyl group, a $C_{3-8}$ cycloalkyl group, a 5- to 10-menbered aromatic heterocyclic group, a $C_{6-13}$ aromatic hydrocarbon-cyclic group, a $C_{4-10}$ heterocyclic group, or a $C_{4-10}$ polycycloalkyl group. W is preferably a single bond or a $C_{1-6}$ alkylene group, and more preferably a single bond.

In the general formula (I) of the compounds of the present invention, Z represents a group represented by the above-described formula Z-1 or Z-2, wherein each of $R^{2a}$ and $R^{2b}$ independently represents a $C_{1-6}$ alkyl group, a $C_{2-6}$ alkenyl group, or a phenyl group, and $Z^2$ represents a sulfur atom or a methine group. Preferably, Z is a group represented by the above-described formula Z-3.

In the present invention, "salt" refers to a pharmacologically acceptable salt, as long as the salt is an addition salt formed with a compound of the present invention. Preferable examples may include, but are not limited to, salts of hydrogen halide acids such as hydrofluorides, hydrochlorides, hydrobromides and hydroiodides; salts of inorganic acids such as sulfates, nitrates, perchlorate, phosphates, carbonates and bicarbonates; salts of organic carboxylic acids such as acetates, oxalates, maleates, tartrates and fumarates; salts of organic sulfonic acids such as methanesulfonates, trifluoromethanesulfonates, ethanesulfonates, benzenesulfonates, toluenesulfonates and camphorsulfonates; salts of amino acids such as aspartates and glutamates; salts with amines such as trimethylamine, triethylamine, procaine, pyridine and phenethylbenzylamine salts; alkali metal salts such as sodium and potassium salts; alkali earth metal salts such as magnesium and calcium salts; and the like.

General Procedures for Synthesis

The following describes typical methods for producing the compounds represented by the above-described formula (I) according to the present invention.

Production Method A:

A method for producing a carbamoylazole derivative (a-3) from an azole derivative (a-1):

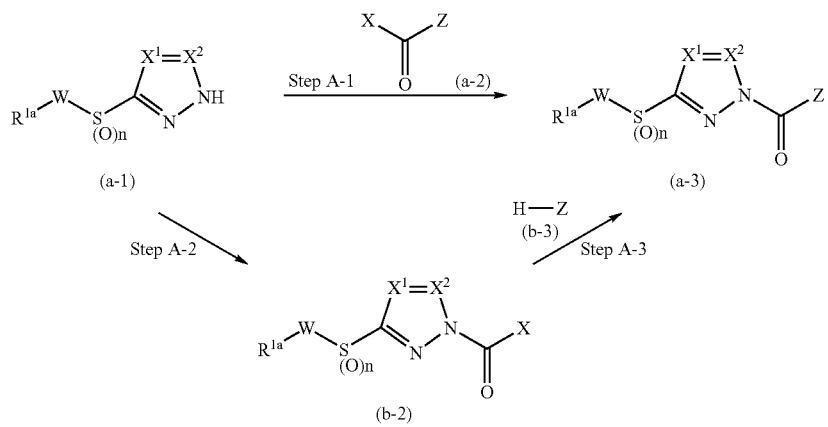

wherein n, W, $X^1$, $X^2$, $R^{1a}$, and Z have the same meaning as defined above. X represents a leaving group such as halogen atoms.

Step A-1 (from (a-1) to (a-3)):

An azole derivative (a-1) can be reacted with a carbamoylating reagent (a-2) to obtain the carbamoylazole derivative (a-3). The reaction is usually carried out in the presence of a base. Examples of the base may include inorganic bases such as anhydrous potassium carbonate, sodium hydrogencarbonate and sodium hydride; organometallic bases such as butyl lithium; and organic bases such as triethylamine. Examples of reaction solvents used in the reaction may include halogenated hydrocarbon solvents such as dichloromethane; ester solvents such as ethyl acetate; ether solvents such as tetrahydrofuran; amide solvents such as N,N-dimethylformamide; and basic solvents such as pyridine. The reaction is usually carried out at a reaction temperature of −78 to 100° C., and preferably −20 to 50° C.

Step A-2 (from (a-1) to (b-2)):

This step is for converting an azole derivative (a-1) into an activated carbonylazole derivative (b-2).

An azole derivative (a-1) can be reacted with a carbonylating reagent (b-1) to obtain the activated carbonylazole derivative (b-2). In this case, the activated carbonylazole derivative (b-2) can be isolated, but in usual cases is used in the subsequent step without its purification. The reaction is usually carried out in the presence of a base. Examples of the base may include inorganic bases such as anhydrous potassium carbonate, sodium hydrogencarbonate and sodium hydride; and organic bases such as triethylamine and pyridine. Examples of carbonylating reagents used in the reaction may include phosgene, phosgene dimer, triphosgene, carbonyldiimidazole and the like. Examples of reaction solvents used in the reaction may include ester solvents such as ethyl acetate, ether solvents such as tetrahydrofuran, amide solvents such as N,N-dimethylformamide, and basic solvents such as pyridine. The reaction is usually carried out at a reaction temperature of −78 to 100° C., and preferably −20 to 25° C.

Step A-3 (from (b-2) to (a-3)):

This step is for converting the activated carbonylazole derivative (b-2) into a carbamoylazole derivative (a-3). The activated carbonylazole derivative (b-2) can be reacted with an organic amine compound (b-3) to obtain the carbamoylazole derivative (a-3). The reaction is usually carried out in the presence of a base. Examples of the base may include inorganic bases such as anhydrous potassium carbonate, sodium hydrogencarbonate and sodium hydride; and organic bases such as triethylamine and pyridine. Examples of reaction solvents used in the reaction may include ester solvents such as ethyl acetate, ether solvents such as tetrahydrofuran, amide solvents such as N,N-dimethylformamide, and basic solvents such as pyridine. The reaction is usually carried out at a reaction temperature of −78 to 100° C., and preferably −20 to 50° C.

Production Method C:

A method for producing a sulfoxide or sulfone derivative compound (b-4).

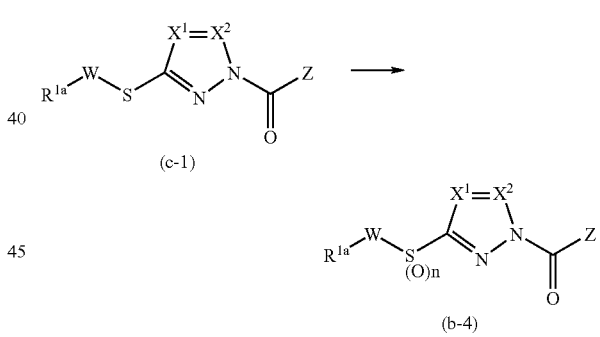

wherein n is 1 or 2; and W, $X^1$, $X^2$, $R^{1a}$, and Z have the same meaning as defined above.

A sulfide derivative (c-1) can be reacted with an appropriate oxidizing agent to obtain the sulfoxide or sulfone derivative (b-4). Examples of the oxidizing agent used in the reaction may include m-chloroperbenzoic acid, hydrogen peroxide, persulfates, percarbonates and the like, and in some cases, salts of metals such as tungsten can be used as a catalyst. Examples of reaction solvents used in the reaction may include ester solvents such as ethyl acetate, halogenated hydrocarbon solvents such as dichloromethane, alcohol solvents such as ethanol, nitrile solvents such as acetonitrile, water, and mixed solvent systems thereof. The reaction temperatures can be used at −20 to 100° C., and preferably at 0 to 60° C. In this step, the sulfoxide or sulfone can be selectively yielded by adjusting the equivalent amount of the oxidizing agent and the reaction conditions.

Production Method D:

A method for producing an aminosulfonylazole derivative (d-3).

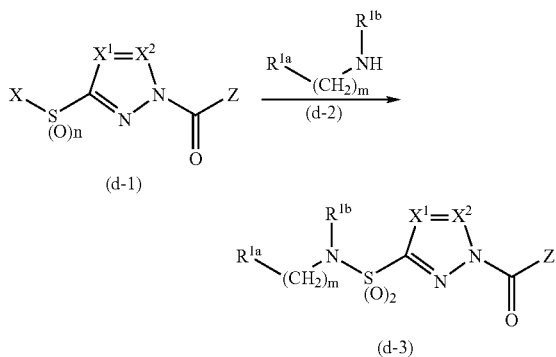

wherein m, $X^1$, $X^2$, $R^{1a}$, $R^{1b}$, and Z have the same meaning as defined above. X represents a leaving group such as halogen atoms.

An activated sulfonylazole derivative (d-1) can be reacted with an organic amine derivative (d-2) to obtain the aminosulfonylazole derivative (d-3). The reaction is usually carried out in the presence of a base. Examples of the base may include organic bases such as triethylamine and pyridine; and inorganic bases such as sodium carbonate, potassium carbonate and sodium hydroxide. Examples of reaction solvents used in the reaction may include ester solvents such as ethyl acetate, ether solvents such as tetrahydrofuran, halogenated hydrocarbon solvents such as dichloromethane, and amide solvents such as N,N-dimethylformamide. The reaction is usually carried out at a reaction temperature of −20 to 50° C., and preferably 0 to 30° C.

Azole derivatives (a-1) used in Step A include intermediates for use in the synthesis of prior art herbicides. For these intermediates, their synthesizing methods are disclosed in their corresponding patents. Here, some examples will be set forth below for reference purposes, but the present invention is not intended to be limited to these examples. In general, synthesis intermediates for carbamoylazole herbicides (azole derivatives) can be used in Step A.

Production Method E:

Steps for converting a mercaptoazole derivative (e-1) to a thioazole derivative (e-3) and further to a sulfinylazole or sulfonyl derivative (e-4).

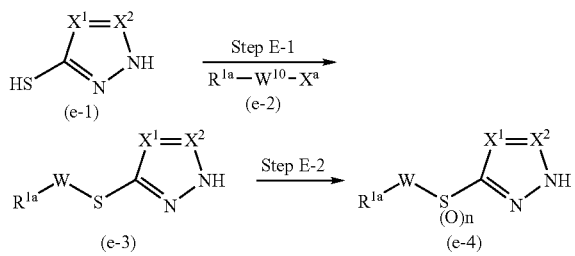

wherein n means 1 or 2, and W, $X^1$, $X^2$, and $R^{1a}$ have the same meaning as defined above. $X^a$ represents a leaving group such as halogen atoms, a methanesulfonyloxy group or para-toluenesulfonyloxy group. $W^{10}$ represents a single bond, a $C_{1-6}$ alkylene group, or a group represented by the formula $W^{10}$-1, wherein m and $R^{1b}$ have the same meaning as defined above.

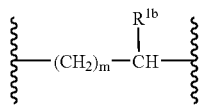

Step E-1 (from (e-1) to (e-3)):

This step is for converting a mercaptoazole derivative (e-1) to a thioazole derivative (e-3).

A mercaptoazole derivative (e-1) can be reacted with an electrophillic compound (e-2) to obtain the thioazole derivative (e-3).

A base can be added to carry out the reaction. Examples of the base may include inorganic bases such as sodium carbonate, potassium carbonate, sodium hydroxide and sodium hydride; and metal alkoxides such as sodium methoxide and potassium t-butoxide. Examples of reaction solvents used in the reaction may include alcohol solvents such as methanol and ethanol, ether solvents such as tetrahydrofuran, amide solvents such as N,N-dimethylformamide, nitrile solvents such as acetonitrile, sulfoxide solvents such as dimethylsulfoxide, basic solvents such as pyridine, or water, or mixed solvent systems thereof. The reaction is carried out at a reaction temperature of −20 to 180° C., and preferably 0 to 150° C.

Step E-2 (from (e-3) to (e-4)):

This step is for converting the thioazole derivative (e-3) to a sulfinylazole or sulfonyl derivative (e-4).

The thioazole derivatives (e-3) can be reacted with an appropriate oxidizing agent to obtain the sulfinylazole or sulfonyl derivative (e-4). The reaction conditions are similar to those in the above-described Production Method C.

Production Method F:

Steps for converting a mercaptoazole derivative (e-1) to a thioazole derivative (f-2) and further to a sulfinylazole or sulfonyl derivative (f-3).

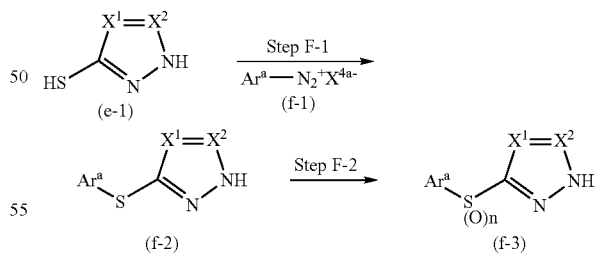

wherein n means 1 or 2, and $X^1$ and $X^2$ have the same meaning as defined above. $X^{4a-}$ represents an anion constituting an acid, such as chloride or sulfate ion, and $Ar^a$ represents an aromatic hydrocarbon cyclic or aromatic heterocyclic group.

Step F-1:

This step is for converting a mercaptoazole derivative (e-1) to a thioazole derivative (f-2).

A mercaptoazole derivative (e-1) can be reacted with a diazonium salt (f-1), which is prepared from an aromatic amine (Ar$^a$—NH$_2$), to obtain the thiazole derivative (f-2). The diazonium salt can be prepared from an aromatic amine in a manner commonly used in the art. In usual cases, the diazonium salt can be prepared by adding dropwise, at a reaction temperature equal to or less than 5° C., an aqueous solution of 1 eq. of a nitrite to an aqueous solution or a mixed solvent of water and an alcohol solvent to which 2 eq. of an acid is added relative to an aromatic amine. The reaction can be carried out by adding the diazonium salt solution or suspension thus prepared to a solution of a mercaptoazole derivative and 2 eq. of a base in water or an alcohol solvent or a mixed solvent thereof at a reaction temperature equal to or less than 5° C. Examples of the acid used in the reaction may include inorganic acid such as hydrochloric acid, sulfuric acid and hydrobromic acid. Examples of the base used in the reaction may include inorganic bases such as sodium hydroxide and potassium hydroxide. The reaction is carried out at a reaction temperature of −20 to 20° C.

Step F-2:

This step is for converting the thiazole derivative (f-2) to a sulfinyl or sulfonyl derivative (f-3). The thiazole derivative (f-2) can be reacted with an appropriate oxidizing agent to obtain the sulfinyl or sulfonyl derivative (f-3). The reaction conditions are similar to those in the above-described Production Method C.

Production Method G:

A step for converting a mercaptoazole derivative (e-1) to a thioazole derivative (g-4).

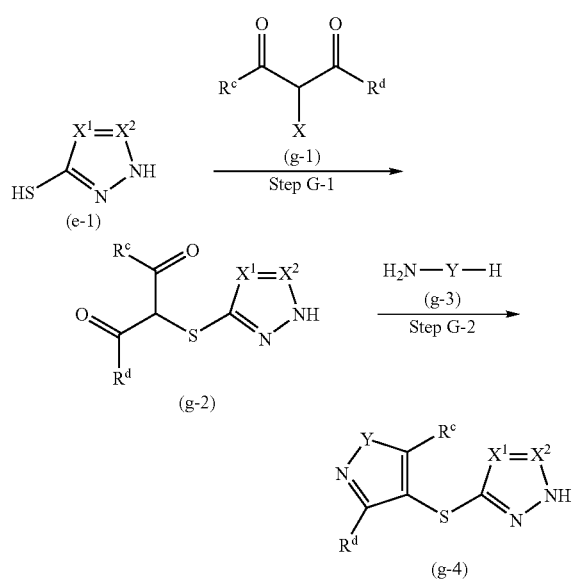

wherein X$^1$ and X$^2$ have the same meaning as defined above. X represents a leaving group such halogen atoms, Y represents O or R$^e$—N. Each of R$^c$, R$^d$ and R$^d$ independently represents the above-described C$_{1-6}$ alkyl groups which may be substituted, the above-described C$_{2-6}$ alkenyl groups which may be substituted, the above-described C$_{2-6}$ alkynyl groups which may be substituted, the above-described C$_{6-14}$ aromatic hydrocarbon cyclic groups which may be substituted, the above-described 4- to 10-membered heterocyclic groups which may be substituted, the above-described 5- to 14-membered aromatic heterocyclic groups which may be substituted, and the above-described C$_{3-8}$ cycloalkyl groups which may be substituted.

Step G-1:

This step is for converting a mercaptoazole derivative (e-1) to a thioazole derivative (g-2).

A mercaptoazole derivative (e-1) can be reacted with a 1,3-dicarbonyl derivative (g-1) to obtain the thioazole derivative (g-2). The reaction can be usually carried out in the presence of a base. Examples of the base used in the reaction may include inorganic bases such as sodium carbonate, potassium carbonate, sodium hydroxide and sodium hydride; and metal alkoxides such as sodium methoxide and potassium t-butoxide. Examples of reaction solvents used in the reaction may include alcohol solvents such as methanol and ethanol, amide solvents such as N,N-dimethylformamide, sulfoxide solvents such as dimethylsulfoxide, ether solvents such as tetrahydrofuran, or water, or mixed solvent systems thereof. The reaction is carried out at a reaction temperature of −20 to 100° C., and preferably 0 to 60° C.

Step G-2:

This step is for converting the thioazole derivative (g-2) to a thioazole derivative (g-4).

The thioazole derivative (g-2) can be reacted with an amine compound (g-3) to obtain the thioazole derivative (g-4). The reaction may or may not employ a base. In the case where the amine compound is a salt, a sufficient amount of a base is used to neutralize it. Examples of the base used in the reaction may include inorganic bases such as sodium hydrogencarbonate and potassium carbonate; and organic bases such as triethylamine. Examples of reaction solvents used in the reaction may include alcohol solvents such as methanol and ethanol, amide solvents such as N,N-dimethylformamide, sulfoxide solvents such as dimethylsulfoxide, ether solvents such as tetrahydrofuran, or water, or mixed solvent systems thereof. The reaction is carried out at a reaction temperature of 0 to 120° C., and preferably 20 to 100° C.

Production Method H;

Steps for converting a mercaptoazole derivative (e-1) to a thioazole derivative (h-3) and further to a sulfinylazole or sulfonyl derivative (h-4).

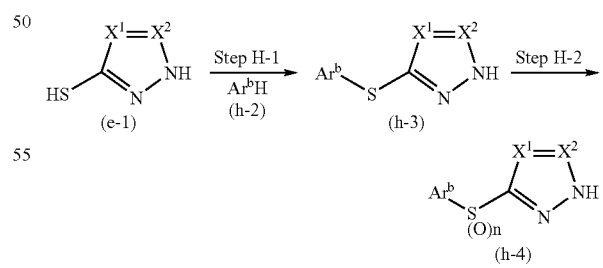

wherein n means 1 or 2, and X$^1$ and X$^2$ have the same meaning as described above. Ar$^b$ represents an aromatic hydrocarbon cyclic group or aromatic heterocyclic group having a high electron density, and thus a group allowing the so-called electrophillic substitution reaction of a hydrogen atom or atoms in Ar$^b$H, such as halogenation and nitration.

Step H-1:

This step is for converting a mercaptoazole derivative (e-1) to a thioazole derivative (h-3).

A mercaptoazole derivative can be reacted with a halogenating agent (h-1), and subsequently with an aromatic compound (h-2), to obtain the thioazole derivative (h-3). The reaction can be usually carried out in the presence of a base. Examples of the base used in the reaction may include metal hydrides such as sodium hydride, and metal alkoxides such as sodium methoxide, sodium ethoxide, and potassium t-butoxide. Examples of the halogenating agent used in the reaction may include halogen molecules such as chlorine molecules and bromine molecules; N-haloimides such as N-chlorosuccucinimide and N-bromosuccucinimide; and the like. Examples of reaction solvents used in the reaction may include alcohol solvents such as methanol and ethanol, and amide solvents such as N,N-dimethylformamide. The reaction is carried out at a reaction temperature of −80 to 150° C., and preferably −70 to 120° C.

Step H-2:

This step is for converting the thioazole derivative (h-3) to a sulfinyl or sulfonyl derivative (h-4). the thioazole derivative (h-3) can be reacted with an appropriate oxidizing agent to obtain the sulfinyl or sulfonyl derivative (h-4). The reaction conditions are similar to those in the above-described Production Method C.

Production Method I:

A step for converting an N-sulfonylazole derivative (i-1) to a C-sulfonylazole derivative (i-3) or (i-4).

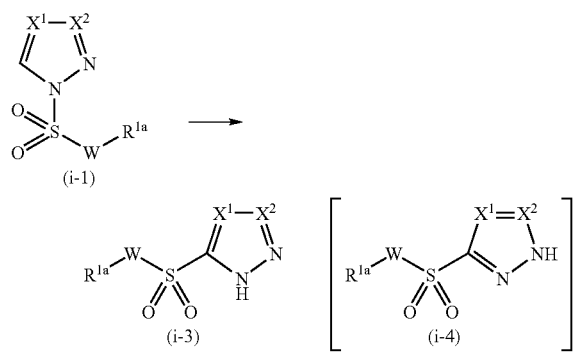

wherein W, $X^1$, $X^2$, and $R^{1a}$ have the same meaning as defined above.

An N-sulfonylazole derivative (i-1) can be reacted with a lithium-attaching reagent (i-2), followed by treatment at an appropriate temperature, to obtain the C-sulfonylazole derivative (i-3), by the rearrangement resulting from reacting. The (i-4) is a tautomer of the (i-3). Examples of the lithium-attaching reagent used in the reaction may include alkyllithiums such as n-butyllithium, sec-butyllithium and t-butyllithium; and lithium amides such as lithium diisopropylamide. Examples of reaction solvents used in the reaction may include ether solvents such as tetrahydrofuran. The reaction is carried out at a reaction temperature of −100 to 100° C., and preferably −78 to 80° C.

Production Method J:

A step for converting a benzylthioazole derivative to a chlorosulfonylazole derivative.

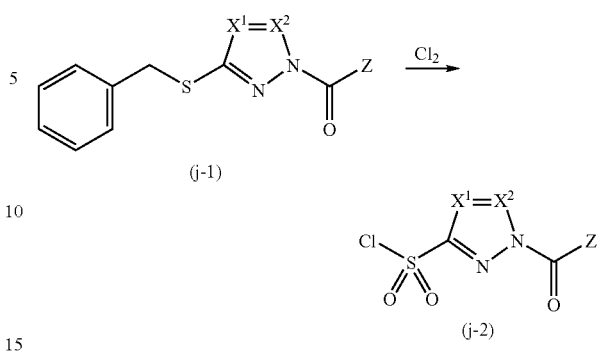

wherein $X^1$, $X^2$, and Z have the same meaning as defined above.

A benzylthioazole derivative (j-1) can be reacted with chlorine to obtain the chlorosulfonylazole derivative (j-2). The reaction can be usually carried out in acetic acid, water, or a mixed solvent thereof, and is achieved by passing 3 to 6 equivalents of chlorine gas. The reaction is usually carried out at a reaction temperature of −10 to 15° C.

Production Method K:

A step for converting a secondary amine compound (b-3) to a carbamoyl chloride (k-2).

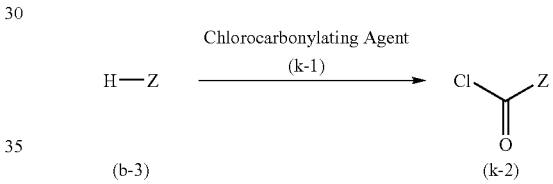

wherein Z has the same meaning as defined above.

A secondary amine compound (b-3) can be reacted with a chlorocarbonylating agent (k-1) to obtain the carbamoyl chloride (k-2). Examples of the chlorocarbonylating agent used in the reaction may include phosgene, phosgene dimer, triphosgene and the like. Examples of the base used in the reaction may include organic bases such as pyridine and triethylamine; and inorganic bases such as anhydrous potassium carbonate.

Various isomers formed with respect to the compounds represented by the above-described formula (I) according to the present invention can be purified and isolated by employing conventional separation means, for example, recrystallization, chromatography, and the like.

The compounds according to the present invention or their salts, or hydrates thereof can be formulated as tablets, powders, fine granules, granules, coated tablets, capsules, syrups, troches, inhalations, suppositories, injections, ointments, eye ointments, eye drops, nasal drops, ear drops, cataplasms, lotions, and the like with methods commonly used in the art. For formulation, it is possible to use formulating aids which are usually employed, for example, excipients, binders, lubricants, coloring agents, corrigents, and optionally stabilizing agents, emulsifiers, absorption enhancers, surfactants, pH adjusting agents, antiseptics, antioxidants, and the like. In general, formulation can be conducted using ordinary methods by incorporating ingredients employed as raw materials of drug preparations. For example, when oral preparations are produced, the compounds according to the present invention or pharmaceutically acceptable salts thereof and excipients, and in addition, optionally binders, disintegrators, lubricants, coloring agents, corrigents, and the like are added and then formed, using usual procedures, into powders, fine granules, granules, tablets, coated tablets, capsules, and the like after adding. These ingredients include, for example, animal and plant oils such soybean oil, beef tallow, and synthetic glycerides; hydrocarbons such as liquid paraffin, squalene, and solid paraffin; ester oils such as octyldodecyl myristate and isopropyl myristate; higher alcohols such as cetostearyl alcohol and behenyl alcohol; silicone resins; silicone oils; surfactants such as polyoxyethylene fatty acid esters, sorbitan fatty acid esters, glycerin fatty acid esters, polyoxyethylene sorbitan fatty acid esters, polyoxyethylene hydrogenated castor oil, and polyoxyethylenepolyoxypropylene block copolymers; water-soluble macromolecules such as hydroxyethylcellulose, poly(acrylic acid), carboxyvinyl polymers, polyethylene glycol, polyvinylpyrrolidone, and methylcellulose; lower alcohols such as ethanol and isopropanol; polyhydric alcohols such as glycerin, propylene glycol, dipropylene glycol, and sorbitol; saccharides such glucose and sucrose; inorganic powders such as silicic acid anhydride, aluminum magnesium silicate, and aluminum silicate; purified water, and the like. As excipients can be employed, for example, lactose, corn starch, white soft sugar, glucose, mannitol, sorbit, crystalline cellulose, silicon dioxide, and the like. As binders can be employed, for example, poly(vinyl alcohol), poly(vinyl ether), methylcellulose, ethylcellulose, acacia gum, tragacanth, gelatin, shellac, hydroxypropylmethylcellulose, hydroxypropylcellulose, polyvinylpyrrolidone, polypropylene glycol polyoxyethylene block copolymers, meglumine, and the like. As disintegrators can be employed, for example, starches, agar, gelatin powder, crystalline cellulose, potassium carbonate, sodium hydrogencarbonate, calcium citrate, dextrin, pectin, carboxymethylcellulose calcium, and the like. As lubricants can be employed, for example, magnesium stearate, talc, polyethylene glycol, silica, hydrogenated plant oils, and the like. As coloring agents can be employed those agents which have been approved for the addition to drugs. As corrigents can be employed, for example, powdered cocoa, menthol, aromatic powders, mentha oil, borneol, powdered cinnamon bark, and the like. Of course, it does not cause any problems that these tables and granules are provided with sugar coatings or other coatings as appropriate, if required. When solutions such as syrups and injectable preparations are produced, they are formulated, using usual procedures, by adding pH adjusting agents, solubilizing agents, tonicity adjusting agents, and the like, and optionally solubilizing aids, stabilizing agents, and the like to the compounds according to the present invention or pharmaceutically acceptable salts thereof. Procedures for producing external preparations are not limited, but they can be prepared using usual procedures. Therefore, as base raw materials for use in their preparation, it is possible to employ various kinds of raw materials which are usually used for drugs, quasi drugs, cosmetics, and the like. Base raw materials to be used include, for example, raw materials such animal and plant oils, mineral oils, ester oils, waxes, higher alcohols, fatty acids, silicone oils, surfactants, phospholipids, alcohols, polyhydric alcohols, water-soluble macromolecules, clay minerals, purified water, and the like, and furthermore, pH adjusting agents, antioxidants, chelators, antiseptic and antifungal agents, coloring agents, flavors, and the like can be added, as required. However, base raw materials for external preparations according to the present invention are not limited to these materials. In addition, it is possible to incorporate, if required, ingredients having differentiation inducing effects, blood-flow enhancing agents, bactericides, antiphlogistics, cell activating agents, vitamins, amino acids, humectants, keratolytics, and the like. The amounts of the above-described base raw materials to be added are usually those providing concentrations which are set up in producing external preparations.

When one administers the compounds according to the present invention or their salts, or hydrates thereof, their forms are not limited specifically, and they can be administered orally or parenterally by means of commonly used procedures. For example, they can be formulated and administered as dosage forms such as tablets, powders, granules, capsules, syrups, troches, inhalations, suppositories, injections, ointments, eye ointments, eye drops, nasal drops, ear drops, cataplasms, lotions, and the like. The amount for administration of the medicaments according to the present invention can be selected as appropriate, depending upon the extend of symptoms, age, sex, weight, the form of administration, the kind of the salt, the particular type of the disease, and the like.

The amount for administration of the DPPIV inhibitors according to the present invention will vary significantly, due to the type of the disease and the extend of symptoms of a patient, age, sex difference, and difference in sensitivity to the agent of the patient, and the like. In usual cases, the DPPIV inhibitors according to the present invention can be administered at doses of about 0.03 to 1000 mg per day with respect to adult humans, and preferably 0.1 to 500 mg, and further preferably 0.1 to 100 mg, divided into one to more portions for a day or for a few days. For injections, the dosage is usually about 1 µg/kg to 3000 µg/kg, and preferably about 3 µg/kg to 1000 µg/kg.

EXAMPLE

The compounds according to the present invention can be prepared, for example, by methods described in the following examples. However, these examples are illustrative and do not intend to limit the compounds according to the present invention, in any way, to specific examples which follows.

Example 1

3-Benzylthio-1-dimethylcarbamoyl-1H-1,2,4-triazole

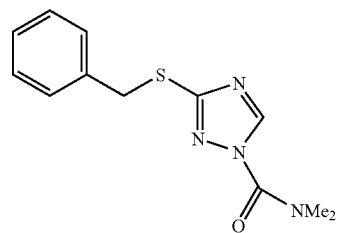

a) 3-Benzylthio-1H-1,2,4-triazole

A solution of 3-mercapto-1H-1,2,4-triazole (100 mg) and benzyl bromide (118 µl) in dimethylformamide (2 ml) was stirred at room temperature for 23 hours. To the reaction mixture were added ethyl acetate and saturated aqueous sodium hydrogencarbonate solution at room temperature, and the resultant mixture was extracted once with ethyl acetate. The organic layer was washed three times with water and subsequently once with saturated aqueous sodium chloride solution, and then dried over anhydrous sodium sulfate. The residue was filtered off, and the solvent was distilled from the resulting filtrate under reduced pressure to yield the titled compound (172 mg) as white solids.

$^1$H-NMR(d6-DMSO) δ=4.35 (2H, s), 7.22–7.31 (3H, m), 7.35–7.38 (2H, m), 8.43 (1H, s).

b)
3-Benzylthio-1-dimethylcarbamoyl-1H-1,2,4-triazole

A suspension of 3-benzylthio-1H-1,2,4-triazole (172 mg), dimethylcarbamoyl chloride (248 μl) and anhydrous potassium carbonate (621 mg) in dimethylformamide (4 ml) was stirred at room temperature for 80 minutes. To the reaction mixture was added water, and the mixture was extracted with ethyl acetate. The organic layer was washed three times with water and subsequently once with saturated aqueous sodium chloride solution, and then dried over sodium sulfate. After filtration, the solvent was distilled from the filtrate under reduced pressure to obtain a clear oil. The resultant oil was purified by a column chromatography (ethyl acetate/hexane=1/5) to yield the titled compound (88 mg) as a clear oil.

$^1$H-NMR (d6-DMSO) δ=3.06 (6H,br s), 4.39 (2H, s), 7.23–7.33 (3H, m), 7.40–7.42 (2H, m), 9.03 (1H,s).

Example 2

3-Benzylsulfonyl-1-dimethylcarbamoyl-1H-1,2,4-triazole

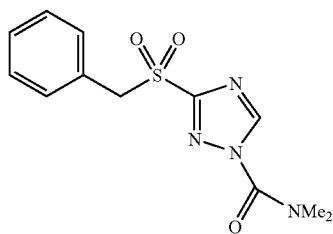

To a solution of 3-benzylthio-1-dimethylcarbamoyl-1H-1,2,4-triazole (Example 1) (134 mg) in methylene chloride was added m-chloroperbenzoic acid (185 mg) with cooling it on ice, and the resulting mixture was stirred at room temperature for 4 hours. Ethyl acetate and water were added to the reaction mixture, which in turn was extracted with ethyl acetate. The organic layer was dried over sodium sulfate, and purified by a column chromatography (ethyl acetate/hexane=1/2) to yield the titled compound (69 mg) as a clear oil.

$^1$H-NMR (d6-DMSO) δ=2.93 (3H,br s), 3.06 (3H,br s), 4.90 (2H, s), 7.25–7.27 (2H, m), 7.33–7.35 (3H, m), 9.35 (1H, s); MS m/e (ESI) 611.15(2M+23).

Example 3

3-Benzylsulfonyl-1-diethylcarbamoyl-1H-1,2,4-triazole

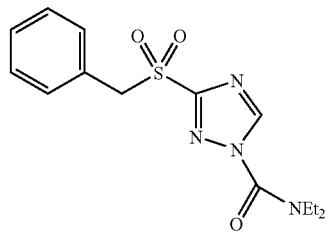

Diethylcarbamoyl chloride was employed to synthesize the title compound as in Examples 1 and 2.
$^1$H-NMR(CDCl$_3$) δ=1.12–1.29 (6H, m), 3.47 (4H,br s), 4.64 (2H, s), 7.25–7.34 (5H, m), 8.88 (1H, br s).

Example 4

3-(4-Fluorobenzyl)sulfonyl-1-dimethylcarbamoyl-1H-1,2,4-triazole

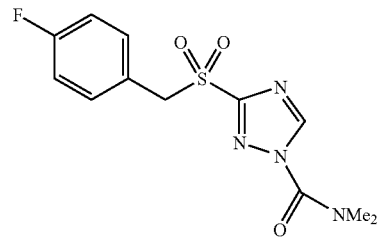

4-Fluorobenzyl bromide was employed to synthesize the title compound as in Examples 1 and 2.
$^1$H-NMR(CDCl$_3$) δ=3.17(6H, s), 4.61(2H, s), 7.02(2H, t, J=9 Hz), 7.28(2H, dd, J=6, 9 Hz), 8.88(1H, s).

Example 5

3-(4-Tert-butylbenzyl)sulfonyl-1-dimethylcarbamoyl-1H-1,2,4-triazole

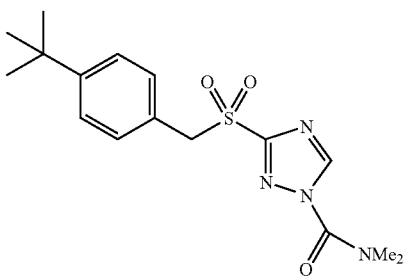

4-Tert-butylbenzyl bromide was employed to synthesize the title compound as in Examples 1 and 2.
$^1$H-NMR(CDCl$_3$) δ=1.27(9H, s), 3.14(6H, s), 4.60(2H, s), 7.20(2H, d, J=8 Hz), 7.33(2H, d, J=8 Hz), 8.87(1H, s).

Example 6

3-(Diphenylmethyl)thio-1-dimethylcarbamoyl-1H-1,2,4-triazole

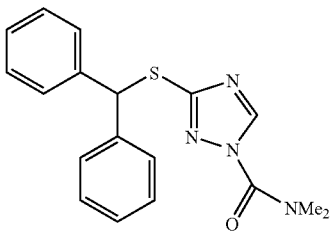

Diphenylmethyl bromide was employed to synthesize the title compound as in Example 1.

$^1$H-NMR(CDCl$_3$) δ=2.84–3.14(6H, br.2peak), 6.08(1H, s), 7.22(2H, t, J=7 Hz), 7.29(4H, t, J=7 Hz), 7.45(4H, d, J=7 Hz), 8.63(1H, s).

Example 7

3-(Diphenylmethyl)sulfonyl-1-dimethylcarbamoyl-1H-1,2,4-triazole

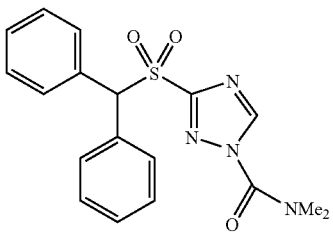

3-(Diphenylmethyl)thio-1-dimethylcarbamoyl-1H-1,2,4-triazole (Example 6) was employed to synthesize the title compound as in Example 2.

$^1$H-NMR(CDCl$_3$) δ=2.97(3H, s), 3.10(3H, s), 5.85(1H, s), 7.30–7.38(6H, m), 7.62(4H, dd, J=2, 7 Hz), 8.73(1H, s).

Example 8

3-[Bis(4-fluorophenyl)methyl]thio-1-dimethylcarbamoyl-1H-1,2,4-triazole

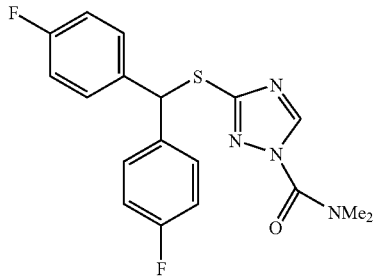

Bis(4-fluorophenyl)methyl chloride was employed to synthesize the title compound as in Example 1.

$^1$H-NMR(CDCl$_3$) δ=3.04(6H, br.s), 6.06(1H, s), 6.99(4H, t, J=9 Hz), 7.39(4H, dd, J=5, 9 Hz), 8.64(1H, s).

Example 9

3-[Bis(4-fluorophenyl)methyl]sulfonyl-1-dimethylcarbamoyl-1H-1,2,4-triazole

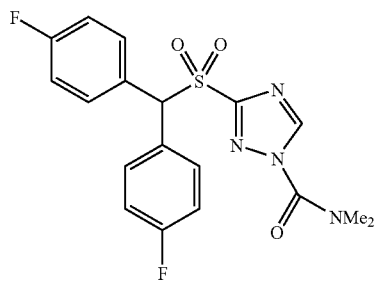

3-[Bis(4-fluorophenyl)methyl]thio-1-dimethylcarbamoyl-1H-1,2,4-triazole (Example 8) was employed to synthesize the title compound as in Example 2.

$^1$H-NMR(CDCl$_3$) δ=3.06(3H, br.s), 3.13(3H, br.s), 5.85 (1H, s), 7.05(4H, t, J=9 Hz), 7.58(4H, dd, J=5, 9 Hz), 8.76(1H, s).

Example 10

3-(Chroman-4-yl)thio-1-dimethylcarbamoyl-1H-1,2,4-triazole

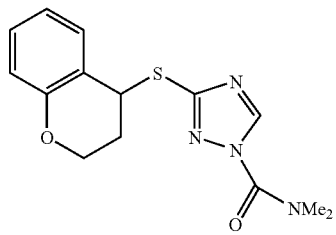

a) 3-(Chroman-4-yl)thio-1H-1,2,4-triazole

To a mixture of triphosgene (95 mg) and dichloromethane (4 ml), with stirring, were added pyridine (82 μl) and 4-chromanol (150 mg) in this order with cooling it on an ice bath. Additional pyridine (82 μl) was added, and the reaction mixture was stirred at room temperature for 2 hours. The reaction solution was added to a mixture of 3-mercapto-1H-1,2,4-triazole (110 mg), anhydrous potassium carbonate (200 mg) and N,N-dimethylformamide (2 ml), and stirred overnight. The reaction solution was washed with water, followed by saturated aqueous sodium chloride solution, and concentrated. The residue was subjected to a silica-gel column chromatography with 50% ethyl acetate/hexane to yield the title compound (110 mg).

$^1$H-NMR(CDCl$_3$) δ=2.25–2.32(1H, m), 2.41–2.51(1H, m), 4.28–4.35(1H, m), 4.42–4.50(1H, m), 5.04(1H, br.s), 6.83(1H, d, J=8 Hz), 6.89(1H, t, J=8 Hz), 7.18(1H, t, J=8 Hz), 7.36(1H, d, J=8 Hz), 8.17(1H, s).

b) 3-(Chroman-4-yl)thio-1-dimethylcarbamoyl-1H-1,2,4-triazole

The title compound was prepared from 3-(chroman-4-yl)thio-1H-1,2,4-triazole in a manner similar to Example 1.

$^1$H-NMR(CDCl$_3$) δ=2.28–2.36(1H, m), 2.42–2.52(1H, m), 3.25(6H, br.s), 4.28–4.35(1H, m), 4.43–4.51(1H, m), 5.05(1H, br.s), 6.83(1H, d, J=8 Hz), 6.90(1H, t, J=8 Hz), 7.17(1H, t, J=8 Hz), 7.38(1H, d, J=8 Hz), 8.78(1H, s).

Example 11

3-(Chroman-4-yl)sulfonyl-1-dimethylcarbamoyl-1H-1,2,4-triazole

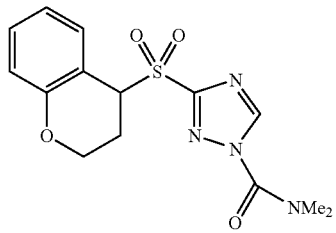

The title compound was prepared from 3-(chroman-4-yl)thio-1-dimethyl-carbamoyl-1H-1,2,4-triazole (Example 10) in a manner similar to Example 2.

$^1$H-NMR(CDCl$_3$) δ=2.28–2.39(1H, m), 2.54–2.62(1H, m), 3.19(3H, br.s), 3.21(3H, br.s), 4.24–4.30(1H, m), 4.54–4.62(1H, m), 4.72–4.76(1H, m), 6.86–6.92(2H, m), 7.25(1H, t, J=8 Hz), 7.35(1H, d, J=8 Hz), 8.91(1H, s).

Example 12

3-(Endo-norbornan-2-yl)thio-1-dimethylcarbamoyl-1H-1,2,4-triazole

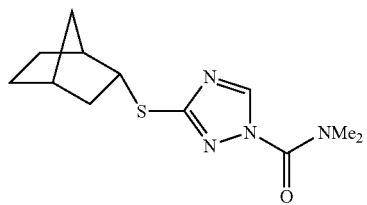

a) 3-(Endo-norbornan-2-yl)thio-1H-1,2,4-triazole

A mixture of 3-mercapto-1H-1,2,4-triazole (5.0 g), exo-2-bromonorbornane (6.4 ml), anhydrous potassium carbonate (10 g) and N,N-dimethylformamide (25 ml) was heated and stirred for 7 hours on an oil bath at 80° C. The reaction solution was extracted with ethyl acetate-water. The organic layer was washed with water, followed by saturated aqueous sodium chloride solution, dried over anhydrous magnesium sulfate, and concentrated under reduced pressure. The residue was subjected to a silica-gel column chromatography with 10 to 20% (20% 2-propanol/ethyl acetate)/hexane to yield the title compound (5.01 g).

$^1$H-NMR(CDCl$_3$) δ=1.01–1.08(1H,m), 1.22–1.30(1H, m), 1.38–1.92(5H, m), 2.14–2.24(1H, m), 2.29(1H, br.s), 2.52(1H, br.s), 3.88–3.95(1H, m), 8.09(1H, s).

b) 3-(Endo-norbornan-2-yl)thio-1-dimethylcarbamoyl-1H-1,2,4-triazole

A mixture of 3-(endo-norbornan-2-yl)thio-1H-1,2,4-triazole (500 mg), dimethylcarbamoyl chloride (0.35 ml), anhydrous potassium carbonate (700 mg) and N,N-dimethylformamide (2 ml) was stirred at room temperature for 5 hours. The reaction solution was extracted with ethyl acetate-water. The organic layer was washed with water, followed by with saturated aqueous sodium chloride solution, dried over anhydrous magnesium sulfate, and concentrated under reduced pressure. The residue was subjected to a silica-gel column chromatography with 10 to 15% (20% 2-propanol/ethyl acetate)/hexane to yield the title compound (650 mg).

$^1$H-NMR(CDCl$_3$) δ=1.02–1.10(1H, m), 1.22–1.31(1H, m), 1.37–1.62(4H, m), 1.83–1.92(1H, m), 2.29(1H, br.s), 2.57(1H, br.s), 3.24(6H, br.s), 3.84–3.92(1H, m), 8.70(1H, s).

Example 13

3-(Endo-norbornan-2-yl)sulfonyl-1-dimethylcarbamoyl-1H-1,2,4-triazole

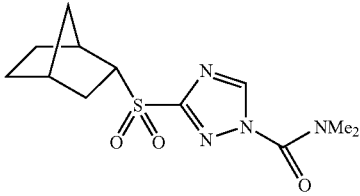

A mixture of 3-(endo-norbornan-2-yl)thio-1-dimethylcarbamoyl-1H-1,2,4-triazole (Example 12) (650 mg), ethyl acetate (5 ml) and m-chloroperbenzoic acid (1.12 g) was stirred at room temperature overnight. One milliliter of 1 M aqueous sodium sulfate solution was added to the reaction solution, which in turn was extracted with ethyl acetate-water. The organic layer was washed with water, followed by saturated aqueous sodium chloride solution, dried over anhydrous magnesium sulfate, and concentrated under reduced pressure. The residue was subjected to a silica-gel column chromatography with 20 to 30% (20% 2-propanol/ethyl acetate)/hexane, and recrystallization was performed in ethyl acetate-hexane to yield the title compound (440 mg).

$^1$H-NMR(CDCl$_3$) δ=1.40–1.70(5H, m), 1.84–1.91(2H, m), 2.27–2.35(1H, m), 2.45(1H, br.s), 2.78(1H, br.s), 3.20 (3H, s), 3.34(3H, s), 3.75–3.82(1H, m), 8.86(1H, s).

The synthesis in the following Examples 14 to 21 was carried out in a manner similar to Examples 12 and 13.

Example 14

3-Cyclohexylthio-1-dimethylcarbamoyl-1H-1,2,4-triazole

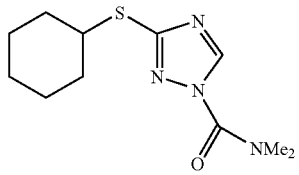

Bromocyclohexane was employed to synthesize the title compound as in Example 12.

$^1$H-NMR(CDCl$_3$) δ=1.24–1.67(6H, m), 1.75–1.84(2H, m), 2.06–2.16(2H, m), 3.00–3.46(6H, br.peak), 3.62(1H, tt, J=4, 10 Hz), 8.72(1H, s).

Example 15

3-Cyclohexylsulfonyl-1-dimethylcarbamoyl-1H-1,2,4-triazole

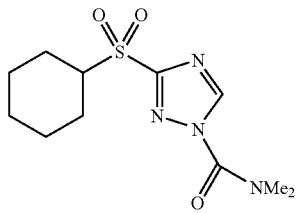

3-Cyclohexylthio-1-dimethylcarbamoyl-1H-1,2,4-triazole (Example 14) was employed to synthesize the title compound as in Example 13.

$^1$H-NMR(CDCl$_3$) δ=1.16–1.76(6H, m), 1.88–1.97(2H, m), 2.09–2.17(2H, m), 3.20(3H, br.s), 3.31(1H, tt, J=4, 12 Hz), 3.34(3H, br.s), 8.89(1H, s).

Example 16

3-Cyclohexylmethylthio-1-dimethylcarbamoyl-1H-1,2,4-triazole

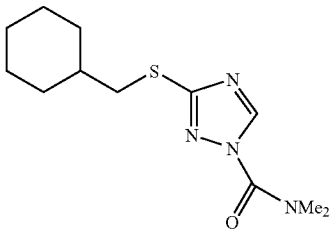

Cyclohexylmethyl bromide was employed to synthesize the title compound as in Example 12.

1H-NMR(CDCl3) δ=0.94–1.30(5H, m), 1.60–1.78(4H, m), 1.85–1.93(2H, m), 3.04(2H, d, J=7 Hz), 3.1–3.4(6H, br. peak), 8.70(1H, s).

Example 17

3-Cyclohexylmethylsulfonyl-1-dimethylcarbamoyl-1H-1,2,4-triazole

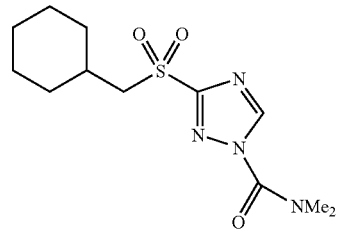

3-Cyclohexylmethylthio-1-dimethylcarbamoyl-1H-1,2,4-triazole (Example 16) was employed to synthesize the title compound as in Example 13.

$^1$H-NMR(CDCl$_3$) δ=–1.05–1.35(5H, m), 1.60–1.74(3H, m), 1.86–1.95(2H, m), 2.04–2.14(1H, m), 3.21(3H, br.s), 3.31(2H, d, J=7 Hz), 3.34(3H, br.s), 8.88(1H, s).

Example 18

3-(1-Adamantylmethyl)thio-1-dimethylcarbamoyl-1H-1,2,4-triazole

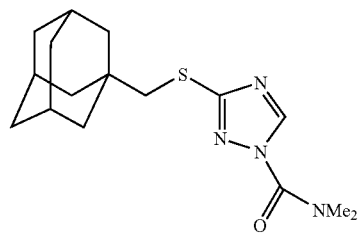

1-Adamantylmethyl methanesulfonate prepared from 1-adamantyl methanol was employed to synthesize the title compound as in Example 12.

1H-NMR(CDCl3) δ=1.58–1.74(12H, m), 1.99(3H, br.s), 3.04(2H, s), 3.12–3.36(6H, br. Peak), 8.70(1H, s).

Example 19

3-(1-Adamantylmethyl)sulfonyl-1-dimethylcarbamoyl-1H-1,2,4-triazole

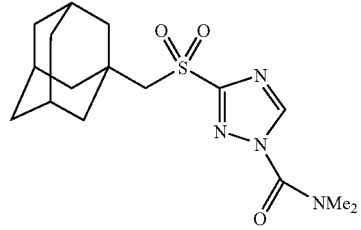

3-(1-Adamantylmethyl)thio-1-dimethylcarbamoyl-1H-1,2,4-triazole (Example 18) was employed to synthesize the title compound as in Example 13.

1H-NMR(CDCl3) δ=1.63–1.74(6H, m), 1.83(6H, d, J=3 Hz), 1.99(3H, br.s), 3.20(3H, br.s), 3.25(2H, s), 3.34(3H, br.s), 8.86(1H, s).

Example 20

3-(3-Methylbutyl)sulfonyl-1-dimethylcarbamoyl-1H-1,2,4-triazole

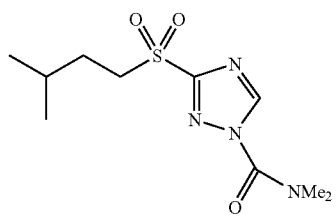

1-Bromo-3-methylbutane was employed to synthesize the title compound as in Examples 12 and 13.

$^1$H-NMR(CDCl$_3$) δ=0.93(6H, d, J=7 Hz), 1.67–1.75(3H, m), 3.20(3H, br.s), 3.34(3H, br.s), 3.36–3.42(2H, m), 8.90 (1H, s).

Example 21

3-(2-Dimethylpropyl)sulfonyl-1-dimethylcarbamoyl-1H-1,2,4-triazole

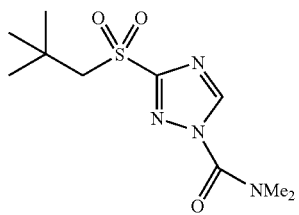

1-Bromo-2,2-dimethylpropane was employed to synthesize the title compound as in Examples 12 and 13.

$^1$H-NMR(CDCl$_3$) δ=1.20(9H, s), 3.20(3H, br.s), 3.34(3H, br.s), 3.38(2H, s), 8.87(1H, s).

Example 22

3-(Endo-norbornan-2-yl)sulfonyl-1-(N-methyl-N-phenylcarbamoyl)-1H-1,2,4-triazole

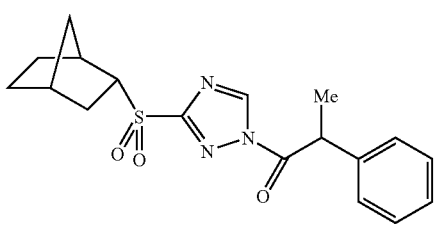

a)
3-(Endo-norbornan-2-yl)sulfonyl-1H-1,2,4-triazole

To a mixture of 3-(endo-norbornan-2-yl)thio-1H-1,2,4-triazole (Example 12-a) (1.0 g) and ethyl acetate (10 ml) was added m-chloroperbenzoic acid (2.4 g) at room temperature, and the reaction mixture was stirred. Heat was generated first, and at the same time when the heat generation ceased, crystals were precipitated. The reaction solution was cooled on ice. The crystals were collected by filtration, washed with ethyl acetate/hexane (1/1), and dried to yield the title compound (1.05 g).

$^1$H-NMR(d$_6$-DMSO) δ=1.22–1.66(6H, m), 1.75–1.85(1H, m), 2.07–2.16(1H, m), 2.34(1H, br.s), 2.54 (1H, br.s), 3.76–3.83(1H, m), 8.88(1H, s).

b) 3-(Endo-norbornan-2-yl)sulfonyl-1-(N-methyl-N-phenylcarbamoyl)-1H-1,2,4-triazole 3-(Endo-norbornan-2-yl)sulfonyl-1H-1,2,4-triazole (100 mg), N-methyl-N-phenylcarbamoyl chloride (75 mg) and anhydrous potassium carbonate (100 mg) were suspended in N,N-dimethylformamide (2 ml) and stirred at room temperature overnight. Water was added to the reaction solution, which in turn was extracted with ethyl acetate. The organic layer was washed with water, followed by saturated aqueous sodium chloride solution, dried over anhydrous magnesium sulfate, and concentrated under reduced pressure. The residue was subjected to a silica-gel column chromatography with 30 to 50% ethyl acetate/hexane to yield the title compound (65 mg).

$^1$H-NMR(CDCl$_3$)δ=1.24–1.44(4H, m), 1.50–1.66(3H, m), 2.08–2.20(1H, m), 2.36(1H, br.s), 2.54(1H, br.s), 3.35 (1H, br.s), 3.55(3H, s), 7.10–7.20(2H, m), 7.30–7.42(3H, m), 8.75(1H, s).

Example 23

3-(Endo-norbornan-2-yl)sulfonyl-1-diallylcarbamoyl)-1H-1,2,4-triazole

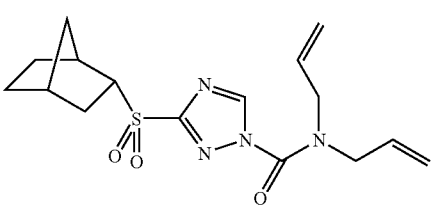

3-(Endo-norbornan-2-yl)sulfonyl-1H-1,2,4-triazole (Example 22-a) and diallylcarbamoyl chloride were employed to synthesize the title compound as in Example 22.

$^1$H-NMR(CDCl$_3$)δ=1.40–1.70(5H, m), 1.83–1.91(2H, m), 2.26–2.35(1H, m), 2.45(1H, br.s), 2.77(1H, br.s), 3.73–3.80(1H, m), 4.00–4.40(4H, m), 5.28(4H, br.s), 5.85–5.96(2H, m), 8.87(1H, s).

Example 24

3-(Endo-norbornan-2-yl)sulfonyl-1-(N-methyl-N-ethylcarbamoyl)-1H-1,2,4-triazole

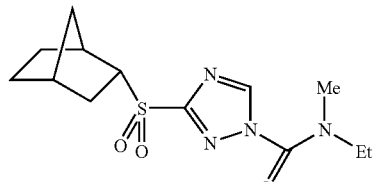

Triphosgene (28 mg) was dissolved in dichloromethane (1 ml). To this solution was added pyridine (0.023 ml) with cooling it on an ice-water bath, and stirring was continued until precipitated materials were dissolved. Then, 3-(endo-norbornan-2-yl)sulfonyl-1H-1,2,4-triazole (Example 22-a) (64 mg) was added, and stirred for additional 20 minutes. Then, N-methylethylamine (0.1 ml) was added, and the reaction mixture was stirred at room temperature. The reaction solution was subjected to a silica-g el column chromatography with 50% ethyl acetate/hexane to yield the title compound (37 mg).

$^1$H-NMR(CDCl$_3$)δ=1.31(3H, br.s), 1.40–1.70(5H, m), 1.80–1.94(2H, m), 2.27–2.36(1H, m), 2.45(1H, br.s), 2.77 (1H, br.s), 3.16(1.3H, br.s), 3.30(1.7H, br.s), 3.50–3.75(2H, m), 3.75–3.82(1H, m), 8.87(1H, br.s).

Example 25

3-(Endo-norbornan-2-yl)sulfonyl-1-(1,3-thiazolidin-3-yl)carbonyl-1H-1,2,4-triazole

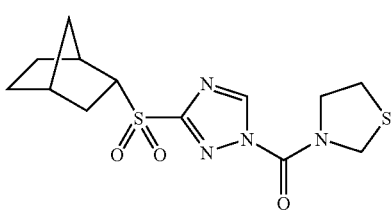

3-(Endo-norbornan-2-yl)sulfonyl-1H-1,2,4-triazole (Example 22-a) and 1,3-thiazolidine were employed to synthesize the title compound as in Example 24.

$^1$H-NMR(CDCl$_3$) δ=1.40–1.71(5H, m), 1.84–1.92(2H, m), 2.26–2.34(1H, m), 2.46(1H, br.s), 2.78(1H, br.s), 3.07–3.21(2H, m), 3.74–3.82(1H, m), 4.00–4.08(1H, m), 4.25–4.35(1H, m), 4.78(1H, br.s), 4.98(1H, br.s), 8.98(1H, s).

Example 26

3-(Endo-norbornan-2-yl)sulfonyl-1-(pyrrolidin-1-yl)carbonyl-1H-1,2,4-triazole

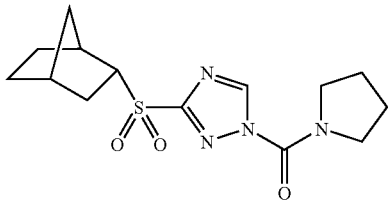

3-(Endo-norbornan-2-yl)sulfonyl-1H-1,2,4-triazole (Example 22-a) and pyrrolidine were employed to synthesize the title compound as in Example 24.

$^1$H-NMR(CDCl$_3$) δ=1.40–1.70(5H, m), 1.84–2.08(6H, m), 2.27–2.36(1H, m), 2.45(1H, br.s), 2.77(1H, br.s), 3.70 (2H, t, J=7 Hz), 3.74–3.82(1H, m), 3.92–4.04(2H, m), 8.96(1H, s).

Example 27

3-(Endo-norbornan-2-yl)sulfonyl-1-(N-methyl-N-allylcarbamoyl)-1H-1,2,4-triazole

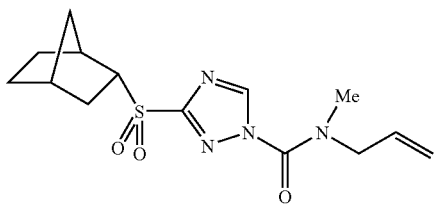

3-(Endo-norbornan-2-yl)sulfonyl-1H-1,2,4-triazole (Example 22-a) and N-methylallylamine were employed to synthesize the title compound as in Example 24.

$^1$H-NMR(CDCl$_3$)δ=1.40–1.70(5H, m), 1.80–1.93(2H, m), 2.26–2.38(1H, m), 2.45(1H, br.s), 2.78(1H, br.s), 3.15 (1.3H, br.s), 3.28(1.7H, br.s), 3.78(1H, br.s), 4.05–4.38(2H, m), 5.20–5.40(2H, m), 5.82–5.97(1H, m), 8.88(1H, br.s).

Example 28

3-(Endo-norbornan-2-yl)sulfonyl-1-(N-methyl-N-propylcarbamoyl)-1H-1,2,4-triazole

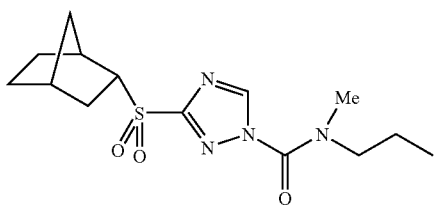

3-(Endo-norbornan-2-yl)sulfonyl-1H-1,2,4-triazole (Example 22-a) and N-methylpropylamine were employed to synthesize the title compound as in Example 24.

1H-NMR(CDCl3)δ=0.85–1.04(3H, m), 1.40–1.80(7H, m), 1.81–1.92(2H, m), 2.27–2.36(1H, m), 2.45(1H, br.s), 2.78(1H, br.s), 3.16(1.8H, br.s), 3.30(1.2H, br.s), 3.50(1.2H, br.s), 3.61(0.8H, br.s), 3.78(1H, br.s), 8.87(1H, s).

Example 29

3-(Endo-norbornan-2-yl)sulfonyl-1-(N-methyl-N-isopropylcarbamoyl)-1H-1,2,4-triazole

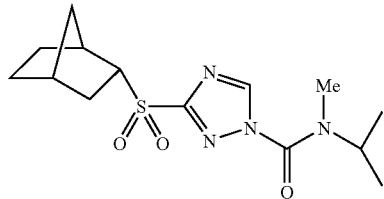

3-(Endo-norbornan-2-yl)sulfonyl-1H-1,2,4-triazole (Example 22-a) and N-methylisopropylamine were employed to synthesize the title compound as in Example 24.

1H-NMR(CDCl3)δ=1.29(6H, d, J=7 Hz), 1.40–1.70(5H, m), 1.85–1.94(2H, m), 2.28–2.37(1H, m), 2.45(1H, br.s), 2.78(1H, br.s), 3.08(3H, br.s), 3.75–3.82(1H, m), 4.60(1H, br.s), 8.84(1H, s).

Example 30

3-(Endo-norbornan-2-yl)sulfonyl-1-(N-methyl-N-isobutylcarbamoyl)-1H-1,2,4-triazole

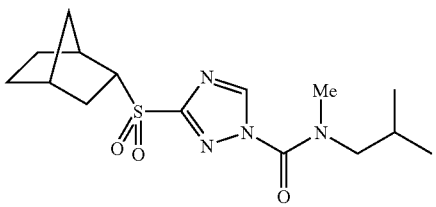

3-(Endo-norbornan-2-yl)sulfonyl-1H-1,2,4-triazole (Example 22-a) and N-methylisobutylamine were employed to synthesize the title compound as in Example 24.

1H-NMR(CDCl3)δ=0.88(2.4H, br.s), 0.99(3.6H, d, J=6 Hz), 1.40–1.70(5H, m), 1.85–2.20(3H, m), 2.28–2.37(1H, m), 2.45(1H, br.s), 2.79(1H, br.s), 3.17(1.2H, br.s), 3.30 (1.8H, br.s), 3.38(1.2H, d, J=7 Hz), 3.60(0.8H, m), 3.78(1H, br.s), 8.86(1H, s).

Example 31

3-(Endo-norbornan-2-yl)sulfonyl-1-(N-methyl-N-tert-butylcarbamoyl)-1H-1,2,4-triazole

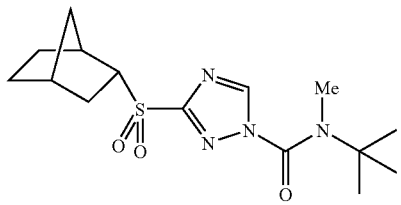

3-(Endo-norbornan-2-yl)sulfonyl-1H-1,2,4-triazole (Example 22-a) and N-methyl-tert-butylamine were employed to synthesize the title compound as in Example 24.

$^1$H-NMR(CDCl$_3$)δ=1.40–1.70(5H, m), 1.51(9H, s), 1.84–1.93(2H, m), 2.27–2.36(1H, m), 2.45(1H, br.s), 2.79 (1H, br.s), 3.02(3H, s), 3.76–3.82(1H, m), 8.77(1H, s).

Example 32

3-(2,4,6-Trimethylphenyl)thio-1-dimethylcarbamoyl-1H-1,2,4-triazole

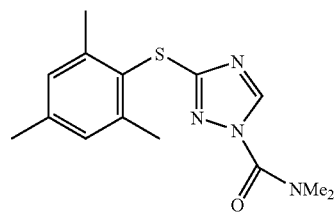

a) 3-(2,4,6-Trimethylphenyl)thio-1H-1,2,4-triazole

While a mixture of 2,4,6-trimethylaniline (13.5 g), methanol (130 ml) and concentrated hydrochloric acid (18.5 ml) was cooled on an ice-sodium chloride bath, a solution of sodium nitrite (6.9 g) in water (10 ml) was slowly added dropwise to the mixture, and the reaction mixture was stirred for 30 minutes as it was.

The above-described reaction solution was added in small portions into a mixture of 2-mercapto-1H-1,2,4-triazole (10.1 g), methanol (70 ml) and potassium hydroxide (13.4 g), which was cooled on an ice-sodium chloride bath. The reaction mixture was stirred at this temperature for 30 minutes, and at room temperature for 1 hour. Concentrated hydrochloric acid (9 ml) was added to the reaction solution, which in turn was extracted with ethyl acetate-water. The organic layer was washed with water, followed by saturated aqueous sodium chloride solution, dried over anhydrous magnesium sulfate, and concentrated under reduced pressure. The residue to which ethyl acetate was added was heated and dissolved. The solution was filtered through a small amount silica gel, and after washing it with ethyl acetate, the filtrate was concentrated under reduced pressure. The residue was crystallized in ethyl acetate-hexane to yield the title compound (12.7 g).

$^1$H-NMR(CDCl$_3$) δ=2.31(3H, s), 2.43(6H, s), 7.04(2H, s), 7.94(1H, s).

b) 3-(2,4,6-Trimethylphenyl)thio-1-dimethylcarbamoyl-1H-1,2,4-triazole

To a mixture of 3-(2,4,6-trimethylphenyl)thio-1H-1,2,4-triazole (220 mg), anhydrous potassium carbonate (280 mg) and N,N-dimethylformamide (1 ml) was added N,N-dimethylcarbamoyl chloride (0.14 ml), and the reaction mixture was stirred at room temperature for 2 hours. The reaction solution was extracted with ethyl acetate-water. The organic layer was washed with water, followed by saturated aqueous sodium chloride solution, dried over anhydrous magnesium sulfate, and concentrated under reduced pressure. The residue was subjected to a silica-gel column chromatography with 10 to 15% (20% 2-propanol/ethyl acetate)/hexane to yield the title compound (276 mg).

$^1$H-NMR(CDCl$_3$) δ=2.29(3H, s), 2.44(6H, s), 3.15(6H, br.s), 6.99(2H, s), 8.63(1H, s).

Example 33

3-(2,4,6-Trimethylphenyl)sulfonyl-1-dimethylcarbamoyl-1H-1,2,4-triazole

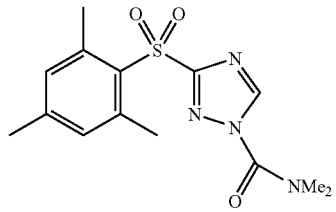

To a mixture of 3-(2,4,6-trimethylphenyl)thio-1-dimethylcarbamoyl-1H-1,2,4-triazole (Example 32) (226 mg) and ethyl acetate (1 ml) was added m-chloroperbenzoic acid (360 mg), and the reaction mixture was heated and stirred for 4 hours on an oil bath at 60° C. To the reaction solution were added 1 M aqueous sodium thiosulfate solution (0.1 ml) and 5 M aqueous potassium carbonate solution (0.25 ml), and the mixture was extracted with ethyl acetate-water. The organic layer was washed with saturated aqueous sodium chloride solution and concentrated. The residue was dissolved in ethyl acetate with heating. The solution was filtered through a small amount silica gel, which was washed with ethyl acetate, and concentrated under reduced pressure. The residue was crystallized in ethyl acetate-hexane to yield the title compound (178 mg).

$^1$H-NMR(CDCl$_3$) δ=2.31(3H, s), 2.70(6H, s), 3.18(3H, br.s), 3.32(3H, br.s), 6.98(2H, s), 8.78(1H, s).

Example 34

3-(2,4,6-Trimethylphenyl)sulfonyl-1-diethylcarbamoyl-1H-1,2,4-triazole

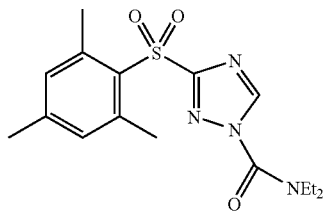

The title compound was synthesized in a manner similar to Examples 32 and 33.

$^1$H-NMR(CDCl$_3$) δ=1.27(6H, t, J=6 Hz), 2.30(3H, s), 2.70(6H, s), 3.51(2H, br.s), 3.61(2H, br.s), 6.97(2H, s), 8.81(1H, s).

Example 35

3-(2,4,6-Trimethylphenyl)sulfonyl-1-(N-methyl-N-phenylcarbamoyl)-1H-1,2,4-triazole

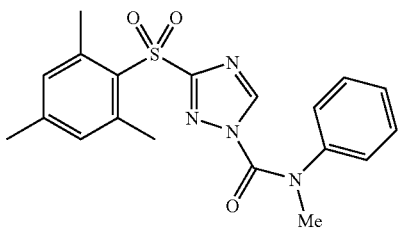

a) 3-(2,4,6-Trimethylphenyl)sulfonyl-1H-1,2,4-triazole

A mixture of OXONE monopersulfate compound (50 g) and water (100 ml) was heated on an oil bath at 60° C., to which was added dropwise a mixture of 3-(2,4,6-trimethylphenyl)thio-1H-1,2,4-triazole (Example 32-a) (5.00 g) and methanol (150 ml) over 1 hour with stirring. After the addition was completed, the reaction mixture was heated and refluxed for 3 hours, and then cooled to room temperature and stirred overnight. Precipitated crystals were collected by filtration, and washed with water to yield the title compound (5.03 g).

$^1$H-NMR(CDCl$_3$)δ=2.31(3H, s), 2.70(6H, s), 6.99(2H, s), 8.54(1H, s).

b) 3-(2,4,6-Trimethylphenyl)sulfonyl-1-(N-methyl-N-phenylcarbamoyl)-1H-1,2,4-triazole 3-(2,4,6-Trimethylphenyl)sulfonyl-1H-1,2,4-triazole and N-methyl-N-phenylcarbamoyl chloride were employed to synthesize the title compound as in Example 22.

$^1$H-NMR(CDCl$_3$)δ=2.30(3H, s), 2.45(6H, s), 3.51(3H, s), 6.89(2H, s), 7.07(2H, br.s), 7.20–7.30(3H, m), 8.71(1H, s).

Example 36

3-(2,4,6-Trimethylphenyl)sulfonyl-1-(N-methyl-N-ethylcarbamoyl)-1H-1,2,4-triazole

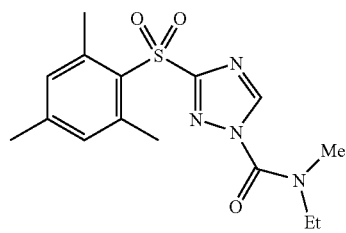

Triphosgene (20 mg) was dissolved in dichloromethane (1 ml). To this solution was added pyridine (0.017 ml) with cooling it on an ice-water bath, and the reaction mixture was stirred for 5 minutes. Then, 3-(2,4,6-trimethylphenyl)sulfonyl-1H-1,2,4-triazole (Example 35-a) (51 mg) was added, and stirred for additional 10 minutes. Then, N-methylethylamine (0.034 ml) was added, and the reaction mixture was stirred at room temperature for 6 hours. The reaction solution was subjected to a silica-gel column chromatography with 50% ethyl acetate/hexane to yield the title compound (52 mg).

$^1$H-NMR(CDCl$_3$)δ=1.28(3H, t, J=7 Hz), 2.31(3H, s), 2.71 (6H, s), 3.13(1.5H, br.s), 3.29(1.5H, br.s), 3.52–3.69(2H, m), 6.98(2H, s), 8.79(1H, s).

Example 37

3-(2,4,6-Trimethylphenyl)sulfonyl-1-(N-methyl-N-propylcarbamoyl)-1H-1,2,4-triazole

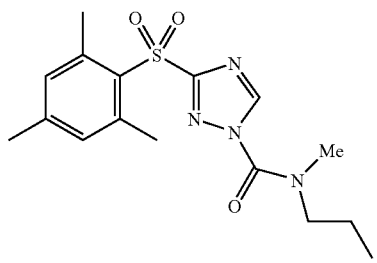

3-(2,4,6-Trimethylphenyl)sulfonyl-1H-1,2,4-triazole (Example 35-a) and N-methylpropylamine were employed to synthesize the title compound as in Example 36.

$^1$H-NMR(CDCl$_3$)δ=0.86(1.5H, br.s), 0.98(1.5H, br.s), 1.71(2H, br.s), 2.31(3H, s), 2.70(6H, s), 3.14(1.5H, br.s), 3.29(1.5H, br.s), 3.48(1H, br.s), 3.56(1H, br.s), 6.98(2H, s), 8.79(1H, s)

Example 38

3-(2,4,6-Trimethylphenyl)sulfonyl-1-(N-methyl-N-isopropylcarbamoyl)-1H-1,2,4-triazole

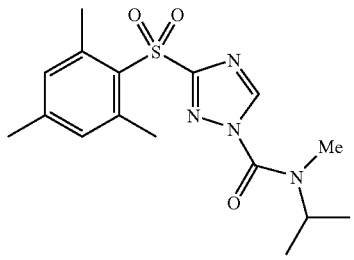

3-(2,4,6-Trimethylphenyl)sulfonyl-1H-1,2,4-triazole (Example 35-a) and N-methylisopropylamine were employed to synthesize the title compound as in Example 36.

$^1$H-NMR(CDCl$_3$)δ=1.27(6H, d, J=7 Hz), 2.31(3H, s), 2.71(6H, s), 2.90–3.15(3H, m), 4.35–4.65(1H, m), 6.97(2H, s), 8.76(1H, s).

Example 39

3-(2,4,6-Trimethylphenyl)sulfinyl-1-dimethylcarbamoyl-1H-1,2,4-triazole

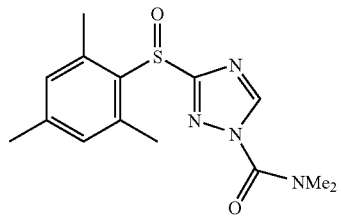

a) 3-(2,4,6-Trimethylphenyl)sulfinyl-1H-1,2,4-triazole

To a mixture of OXONE monopersulfate compound (3.02 g) and water (30 ml) was added dropwise a mixture of 3-(2,4,6-trimethylphenyl)thio-1H-1,2,4-triazole (Example 32-a) (1.08 g) and methanol (30 ml) with stirring it at room temperature. After the addition was completed, the reaction mixture was stirred for 3 hours, and water (20 ml) was added. Precipitated crystals were collected by filtration, and washed with water, ethyl acetate, and hexane in this order to yield the title compound (820 mg).

$^1$H-NMR(DMSO-d6) δ=2.26(3H, s), 2.45(6H, s), 6.95 (2H, s), 8.68(1H, br.s).

b) 3-(2,4,6-Trimethylphenyl)sulfinyl-1-dimethylcarbamoyl-1H-1,2,4-triazole 3-(2,4,6-Trimethylphenyl)sulfinyl-1H-1,2,4-triazole and dimethylcarbamoyl chloride were employed to synthesize the title compound as in Example 22.

$^1$H-NMR(CDCl$_3$)δ=2.30(3H, s), 2.54(6H, s), 3.17(3H, br.s), 3.34(3H, br.s), 6.91(2H, s), 8.78(1H, s).

Example 40

3-[2-(2,2,2-Trifluoroethyl)oxy-6-methylphenyl]thio-1-dimethylcarbamoyl-1H-1,2,4-triazole

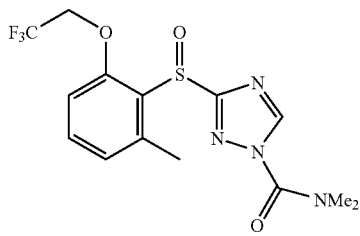

a) 2,2,2-Trifluoroethyl methanesulfonate

To a mixture of 2,2,2-trifluoroethanol (5 g), triethylamine (14 ml) and ethyl acetate (120 ml) was added dropwise methanesulfonyl chloride (5.8 ml) with cooling it on ice, and stirred at this temperature for 1 hour. The reaction solution was filtered through a small amount of silica gel, followed by NH silica gel, which in turn was washed with ethyl acetate. The filtrate was concentrated under reduced pressure to yield the title compound (9.5 g).

$^1$H-NMR(CDCl$_3$) δ=3.15(3H, s), 4.54(2H, q, J=8 Hz).

b) 2-Nitro-3-(2,2,2-Trifluoroethyl)oxytoluene

A mixture of 3-hydroxy-2-nitrotoluene (5 g), 2,2,2-trifluoroethyl methanesulfonate (8.7 g), anhydrous potassium carbonate (9 g) and N,N-dimethylformamide (40 ml) was heated, with stirring, on an oil bath at 80° C. for 4 hours, and then at 100° C. for 4 hours. The reaction solution was extracted with ethyl acetate-water. The organic layer was washed with water, followed by a dilute aqueous potassium carbonate solution and then saturated aqueous sodium chloride solution, and dried over anhydrous magnesium sulfate, and then filtered through NH silica gel, which was washed with ethyl acetate. The filtrate was concentrated under reduced pressure, and subjected to a silica-gel column chromatography with 5 to 10% ethyl acetate/hexane to yield the title compound (4.12 g).

$^1$H-NMR(CDCl$_3$) δ=2.33(3H, s), 4.42(2H, q, J=8 Hz), 6.89(1H, d, J=8 Hz), 6.99(1H, d, J=8 Hz), 7.34(1H, t, J=8 Hz).

c) 2-Amino-3-(2,2,2-trifluoroethyl)oxytoluene

To a mixture of 2-nitro-3-(2,2,2-trifluoroethyl)oxytoluene (4.12 g) and ethyl acetate (30 ml) was added a catalytic amount of 10% palladium/carbon. Then, the mixture was stirred under a hydrogen atmosphere for 4 hours. The catalyst was removed from the reaction solution by filtration, and the filtrate was concentration under reduced pressure to yield the title compound (3.71 g).

$^1$H-NMR(CDCl$_3$) δ=2.19(3H, s), 3.79(2H, br.s), 4.36(2H, q, J=8 Hz), 6.62–6.70(2H, m), 6.80(1H, dd, J=2, 7 Hz).

d) 3-[2-(2,2,2-Trifluoroethyl)oxy-6-methylphenyl]thio-1-dimethyl-carbamoyl-1H-1,2,4-triazole 2-Amino-3-(2,2,2-trifluoroethyl)oxytoluene was employed to synthesize the title compound as in Example 32.

$^1$H-NMR(CDCl$_3$) δ=2.51(3H, s), 3.17(6H, br.s), 4.32(2H, q, J=8 Hz), 6.80(1H, d, J=8 Hz), 7.06(1H, d, J=8 Hz), 7.31(1H, t, J=8 Hz), 8.62(1H, s).

Example 41

3-[2-(2,2,2-Trifluoroethyl)oxy-6-methylphenyl]sulfonyl-1-dimethyl-carbamoyl-1H-1,2,4-triazole

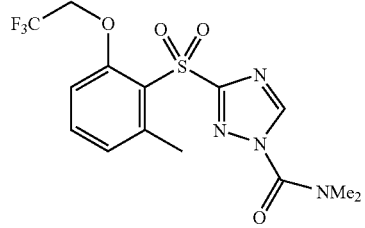

3-[2-(2,2,2-Trifluoroethyl)oxy-6-methylphenyl]thio-1-dimethylcarbamoyl-1H-1,2,4-triazole (Example 40) was employed to synthesize the title compound as in Example 33.

$^1$H-NMR(CDCl$_3$) δ=2.84(3H, s), 3.19(3H, br.s), 3.35(3H, br.s), 4.32(2H, q, J=8 Hz), 6.84(1H, d, J=8 Hz), 7.09(1H, d, J=8 Hz), 7.49(1H, t, J=8 Hz), 8.78(1H, s).

Example 42

3-[2-(2-Methoxyethyl)oxy-6-methylphenyl]thio-1-dimethylcarbamoyl-1H-1,2,4-triazole

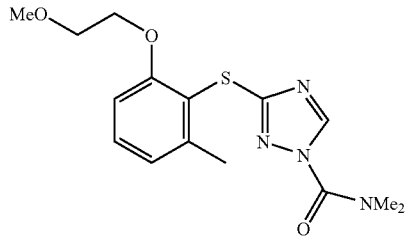

2-Bromoethyl methyl ether was employed to synthesize the title compound as in Example 40.

$^1$H-NMR(CDCl$_3$) δ=2.48(3H, s), 3.14(6H, br.s), 3.33(3H, s), 3.61(2H, t, J=5 Hz), 4.07(2H, t, J=5 Hz), 6.80(1H, d, J=8 Hz), 6.94(1H, d, J=8 Hz), 7.27(1H, t, J=8 Hz), 8.63(1H, s).

Example 43

3-[2-(2-Methoxyethyl)oxy-6-methylphenyl]sulfonyl-1-dimethylcarbamoyl-1H-1,2,4-triazole

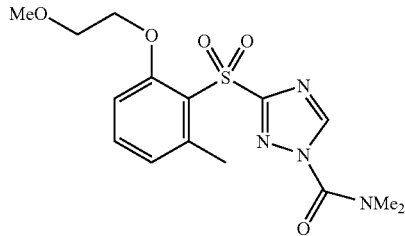

3-[2-(2-Methoxyethyl)oxy-6-methylphenyl]thio-1-dimethylcarbamoyl-1H-1,2,4-triazole (Example 42) was employed to synthesize the title compound as in Example 33.

$^1$H-NMR(CDCl$_3$) δ=2.81(3H, s), 3.17(3H, br.s), 3.25(3H, s), 3.31(3H, br.s), 3.49(2H, t, J=5 Hz), 4.01(2H, t, J=5 Hz), 6.82(1H, d, J=8 Hz), 6.94(1H, d, J=8 Hz), 7.42(1H, t, J=8 Hz), 8.77(1H, s).

Example 44

3-(4-Cyano-2,5-difluorophenyl)thio-1-dimethylcarbamoyl-1H-1,2,4-triazole

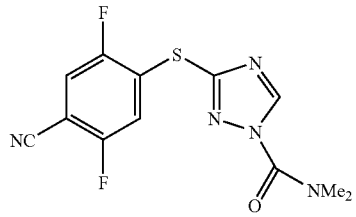

A mixture of 2,4,5-trifluorobenzonitrile (1.6 g), 3-mercapto-1H-1,2,4-triazole (1.2 g), anhydrous potassium carbonate (2.1 g) and N,N-dimethylformamide (10 ml) was stirred at room temperature for 2 hours. The reaction solution was extracted with ethyl acetate-water. The organic layer was washed with water, followed by saturated aqueous sodium chloride solution, dried over anhydrous magnesium sulfate, and concentrated under reduced pressure. The residue was dried in vacuo, to obtain solid material (2.06 g) which gave 2 spots by thin-layer chromatography.

To a mixture of this crystal (240 mg), anhydrous potassium carbonate (280 mg) and N,N-dimethylformamide (1 ml) was added dimethylcarbamoyl chloride (0.14 ml), and the reaction mixture was stirred at room temperature for 1 hour. The reaction solution was extracted with ethyl acetate-water. The organic layer was washed with water, followed by saturated aqueous sodium chloride solution, and then concentrated. The residue was subjected twice to a silica-gel chromatography with 15 to 20% (20% 2-propanol/ethyl acetate)/hexane to yield the title compound (114 mg) which corresponded to the spot changed on the thin-layer chromatogram.

$^1$H-NMR(CDCl$_3$) δ=3.20(3H, br.s), 3.29(3H, br.s), 7.36 (1H, dd, J=5, 8 Hz), 7.42(1H, dd, J=5, 8 Hz), 8.84(1H, s).

Example 45

3-(4-Cyano-2,5-difluorophenyl)sulfonyl-1-dimethylcarbamoyl-1H-1,2,4-triazole

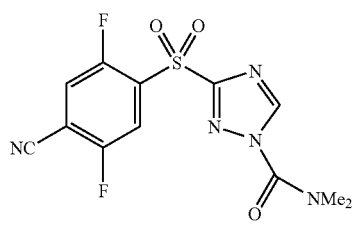

3-(4-Cyano-2,5-difluorophenyl)thio-1-dimethylcarbamoyl-1H-1,2,4-triazole (Example 44) was employed to synthesize the title compound as in Example 33.

$^1$H-NMR(CDCl$_3$) δ=3.21(3H, s), 3.33(3H, s), 7.51(1H, dd, J=5, 8 Hz), 8.05(1H, dd, J=5, 7 Hz), 8.86(1H, s).

Example 46

3-(3,5-Dimethylisoxazol-4-yl)thio-1-dimethylcarbamoyl-1H-1,2,4-triazole

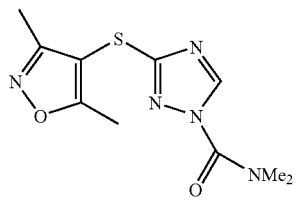

a) 3-(2,4-Pentanedion-3-yl)thio-1H-1,2,4-triazole

To a solution of potassium hydroxide (13 g) in methanol (200 ml), with cooling it on ice, was added 3-mercapto-1H-1,2,4-triazole (20 g), followed by 3-chloro-2,4-pentanedione (24 ml). Then, mixture was stirred at room temperature overnight. Insoluble materials in the reaction solution were filtered off, and the filtrate was concentrated under reduced pressure. The residue was extracted with ethyl acetate-water. The organic layer was washed with saturated aqueous sodium chloride solution, dried over anhydrous magnesium sulfate, and then filtered through a small amount of silica gel, which was washed with ethyl acetate. The filtrate was concentrated under reduced pressure. The residue was recrystallized in ethyl acetate-hexane to yield the title compound (33.1 g).

$^1$H-NMR(CDCl$_3$) δ=2.42(6H, s), 8.15(1H, s).

b) 3-(3,5-Dimethylisoxazol-4-yl)thio-1H-1,2,4-triazole

A mixture of 3-(2,4-pentanedion-3-yl)thio-1H-1,2,4-triazole (2 g), hydroxylamine hydrochloride (0.7 g), triethylamine (1.4 ml) and ethanol (10 ml) was heated and stirred for 5 hours on an oil bath at 100° C. The reaction solution was concentrated under reduced pressure, and then extracted with ethyl acetate-water. The organic layer was washed with saturated aqueous sodium chloride solution, dried over anhydrous magnesium sulfate, and concentrated under reduced pressure. The residue was subjected to a silica-gel column chromatography with 10 to 30% (20% 2-propanol/ ethyl acetate)/hexane, followed by recrystallization in ethyl acetate-hexane to yield the title compound (440 mg).

$^1$H-NMR(CDCl$_3$) δ=2.28(3H, s), 2.50(3H, s), 8.14(1H, s).

c) 3-(3,5-Dimethylisoxazol-4-yl)thio-1-dimethylcarbamoyl-1H-1,2,4-triazole 3-(3,5-Dimethylisoxazol-4-yl)thio-1H-1,2,4-triazole was employed to synthesize the title compound as in Example 32.

$^1$H-NMR(CDCl$_3$) δ=2.28(3H, s), 2.49(3H, s), 3.17(6H, br.s), 8.69(1H, s).

Example 47

3-(3,5-Dimethylisoxazol-4-yl)sulfonyl-1-dimethyl-carbamoyl-1H-1,2,4-triazole

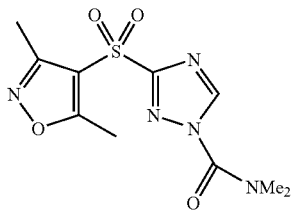

3-(3,5-Dimethylisoxazol-4-yl)thio-1-dimethylcarbamoyl-1H-1,2,4-triazole (Example 46) was employed to synthesize the title compound as in Example 33

$^1$H-NMR(CDCl$_3$) δ=2.50(3H, s), 2.76(3H, s), 3.20(3H, br.s), 3.33(3H, br.s), 8.83(1H, s).

Example 48

3-(3,5-Dimethyl-1-phenylpyrazol-4-yl)thio-1-dimethylcarbamoyl-1H-1,2,4-triazole

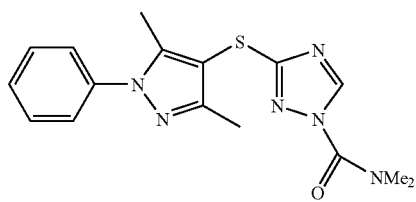

a) 3-(3,5-Dimethyl-1-phenylpyrazol-4-yl)thio-1H-1,2,4-triazole

A mixture of 3-(2,4-pentanedion-3-yl)thio-1H-1,2,4-triazole (Example 46-a) (2 g), phenylhydrazine (1 ml) and ethanol (10 ml) was heated and stirred for 4 hours on an oil bath at 100° C. The reaction solution was concentrated under reduced pressure, and then the residue was crystallized from ethanol-ethyl acetate to yield the title compound (1.42 g).

$^1$H-NMR(d6-DMSO) δ=2.21(3H, s), 2.35(3H, s), 7.40–7.56(5H, m).

b) 3-(3,5-Dimethyl-1-phenylpyrazol-4-yl)thio-1-dimethylcarbamoyl-1H-1,2,4-triazole 3-(3,5-Dimethyl-1-phenylpyrazol-4-yl)thio-1H-1,2,4-triazole was employed to synthesize the title compound as in Example 32.

$^1$H-NMR(CDCl$_3$) δ=2.35(3H, s), 2.40(3H, s), 3.18(6H, br.s), 7.36–7.51(5H, m), 8.69(1H, s).

Example 49

3-(3,5-Dimethyl-1-phenylpyrazol-4-yl)sulfonyl-1-dimethylcarbamoyl-1H-1,2,4-triazole

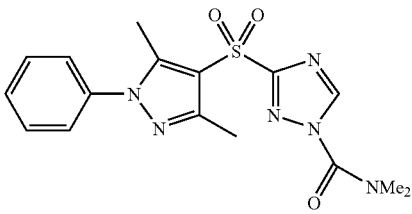

3-(3,5-Dimethyl-1-phenylpyrazol-4-yl)thio-1-dimethylcarbamoyl-1H-1,2,4-triazole (Example 48) was employed to synthesize the title compound as in Example 33.

$^1$H-NMR(CDCl$_3$) δ=2.55(3H, s), 2.60(3H, s), 3.20(3H, br.s), 3.35(3H, br.s), 7.36–7.54(5H, m), 8.82(1H, s).

Example 50

3-(2-Methylimidazo[1,2-a]pyridin-3-yl)thio-1-dimethylcarbamoyl-1H-1,2,4-triazole

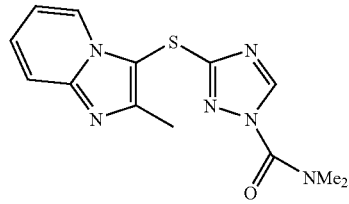

a) 2-Methylimidazo[1,2-a]pyridine

A mixture of 2-aminopyridine (9.4 g), chloroacetone (9.5 ml), and ethanol (25 ml) was heated and stirred for 5 hours on an oil bath at 100° C. After that, the reaction solution was concentrated under reduced pressure, and extracted with ethyl acetate-aqueous potassium carbonate solution. The organic layer was washed with saturated aqueous sodium chloride solution, dried over anhydrous magnesium sulfate, and then concentrated under reduced pressure. The residue was subjected to a column chromatography using NH silica gel with 20 to 30% ethyl acetate/hexane to yield the title compound (5.5 g).

$^1$H-NMR(CDCl$_3$) δ=2.46(3H, s), 6.72(1H, dt, J=1, 7 Hz), 7.10(1H, ddd, J=1, 7, 9 Hz), 7.33(1H, s), 7.50(1H, dt, J=9, 1 Hz), 8.03(1H, dt, J=7, 1 Hz).

b) 3-(2-Methylimidazo[1,2-a]pyridin-3-yl)thio-1H-1,2,4-triazole

To a mixture of 3-mercapto-1H-1,2,4-triazole (1.15 g) and N,N-dimethylformamide (15 ml) was added 60% sodium hydride (450 mg). After foaming was completed, N-chlorosuccinimide in small portions was added to the mixture on an ice bath, and stirred at this temperature for 15 minutes. 2-methylimidazo[1,2-a]pyridine (1.0 g) was then added, and the reaction mixture was heated and stirred at room temperature for 1 hour, and then for 3 hours on an oil bath at 70° C. The reaction solution was concentrated under reduced pressure. The residue was washed twice with diethyl ether, and methanol was added to the residue to remove undissolved materials. The filtrate was concentrated, and then crystals precipitated by the addition of water were collected by filtration, washed with water, followed by diethyl ether, and dried to yield the title compound (480 mg).

$^1$H-NMR(d6-DMSO) δ=2.43(3H, s), 7.02(1H, dt, J=1, 7 Hz), 7.39(1H, ddd, J=1, 7, 9 Hz), 7.58(1H, d, J=9 Hz), 8.38(1H, d, J=7 Hz), 8.49(1H, br.s), 14.10(1H, br.s).

c) 3-(2-Methylimidazo[1,2-a]pyridin-3-yl)thio-1-dimethylcarbamoyl-1H-1,2,4-triazole 3-(2-Methylimidazo[1,2-a]pyridin-3-yl)thio-1H-1,2,4-triazole was employed to synthesize the title compound as in Example 32.

$^1$H-NMR(CDCl$_3$) δ=2.58(3H, s), 3.04(6H, s), 6.88(1H, dt, J=1, 7 Hz), 7.29(1H, ddd, J=1, 7, 9 Hz), 7.59(1H, dt, J=9, 1 Hz), 8.28(1H, dt, J=7, 1 Hz), 8.65(1H, s).

Example 51

3-(2-Methylimidazo[1,2-a]pyridin-3-yl)sulfonyl-1-dimethylcarbamoyl-1H-1,2,4-triazole

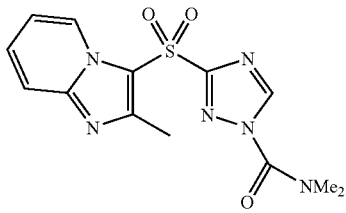

a) 3-(2-Methylimidazo[1,2-a]pyridin-3-yl)sulfonyl-1H-1,2,4-triazole

To a mixture of 3-(2-methylimidazo[1,2-a]pyridin-3-yl)thio-1H-1,2,4-triazole (Example 50-a) (230 mg), acetonitrile (5 ml) and water (5 ml) was added sodium percarbonate (630 mg) in small portions on a water bath at 30° C. At this temperature the reaction mixture was stirred for 4 hours. To the reaction solution was added water (7.5 ml), and then concentrated hydrochloric acid was added dropwise on an ice bath, followed by adjusting the pH to about 4. The reaction mixture was stirred as it was for 30 minutes, and precipitated crystals were collected by filtration, washed with water, and dried to the title compound (139 mg).

$^1$H-NMR(d6-DMSO) δ=2.62(3H, s), 7.27(1H, dt, J=1, 7 Hz), 7.62(1H, ddd, J=1, 7, 9 Hz), 7.73(1H, dt, J=9, 1 Hz), 8.80(1H, s), 8.86(1H, dt, J=7, 1 Hz).

b) 3-(2-Methylimidazo[1,2-a]pyridin-3-yl)sulfonyl-1-dimethylcarbamoyl-1H-1,2,4-triazole To a mixture of 3-(2-methylimidazo[1,2-a]pyridin-3-yl)sulfonyl-1H-1,2,4-triazole (100 mg), anhydrous potassium carbonate (105 mg) and N,N-dimethylformamide (0.5 ml) was added dimethylcarbamoyl chloride (0.06 ml), and the reaction mixture was stirred at room temperature overnight. The reaction solution was extracted with ethyl acetate-water. The organic layer was washed with water, followed by saturated aqueous sodium chloride solution, and concentrated. The residue was subjected to a silica-gel column chromatography with 30 to 50% (20% 2-propanol/ethyl acetate)/hexane to yield the title compound (107 mg).

$^1$H-NMR(CDCl$_3$) δ=2.79(3H, s), 3.17(3H, br.s), 3.29(3H, br.s), 7.05(1H, dt, J=1, 7 Hz), 7.48(1H, ddd, J=1, 7, 9 Hz), 7.65(1H, dt, J=9, 1 Hz), 8.77(1H, s), 9.04(1H, dt, J=1, 7 Hz).

Example 52

3-(6-Bromo-2-pyridyl)thio-1-dimethylcarbamoyl-1H-1,2,4-triazole

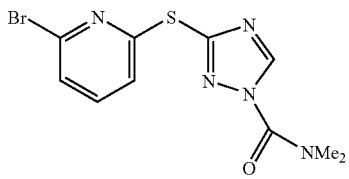

a) 3-(6-Bromo-2-pyridyl)thio-1H-1,2,4-triazole

A mixture of 3-mercapto-1H-1,2,4-triazole (200 mg), 2,6-dibromopyridine (560 mg), anhydrous potassium carbonate (420 mg) and N,N-dimethylformamide (1 ml) was heated and stirred for 3 hours on an oil bath at 100° C. The reaction solution was extracted with ethyl acetate-water. The organic layer was washed with water, followed by saturated aqueous sodium chloride solution, dried over anhydrous magnesium sulfate, and concentrated under reduced pressure. The residue was purified by a silica-gel column chromatography with 5 to 30% (20% 2-propanol/ethyl acetate)/hexane to yield the title compound (73 mg).

$^1$H-NMR(CDCl$_3$) δ=7.34(1H, d, J=8 Hz), 7.40(1H, d, J=8 Hz), 7.53(1H, t, J=8 Hz), 8.12(1H, s).

b) 3-(6-Bromo-2-pyridyl)thio-1-dimethylcarbamoyl-1H-1,2,4-triazole

A mixture of 3-(6-bromo-2-pyridyl)thio-1H-1,2,4-triazole (73 mg), dimethylcarbamoyl chloride (40 µl), anhydrous potassium carbonate (80 mg) and N,N-dimethylformamide (0.5 ml) was stirred at room temperature for 2 hours. The reaction solution was extracted with ethyl acetate-water. The organic layer was washed with water, followed by saturated aqueous sodium chloride solution, dried over anhydrous magnesium sulfate, and concentrated under reduced pressure. The residue was purified by a silica-gel column chromatography with 20% (20% 2-propanol/ethyl acetate)/hexane to yield the title compound (77 mg).

$^1$H-NMR(CDCl$_3$) δ=3.19(3H, br.s), 3.33(3H, br.s), 7.31 (1H, dd, J=1, 8 Hz), 7.34(1H, dd, J=1, 8 Hz), 7.44(1H, t, J=8 Hz), 8.85(1H, s).

Example 53

3-(6-Bromo-2-pyridyl)sulfonyl-1-dimethylcarbamoyl-1H-1,2,4-triazole

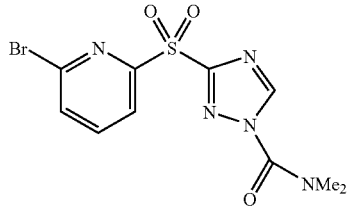

To a mixture of 3-(6-bromo-2-pyridyl)thio-1-dimethylcarbamoyl-1H-1,2,4-triazole (Example 52) (60 mg) and ethyl acetate (0.5 ml) was added m-chloroperbenzoic acid (84 mg), and the reaction mixture was heated and stirred for 2 hours on an oil bath at 60° C. To the reaction mixture was added hexane (0.5 ml), and crystals were collected at room temperature by filtration, washed with ethyl acetate/hexane (1/1), and dried to yield the title compound (45 mg).

$^1$H-NMR(CDCl$_3$) δ=3.20(3H, s), 3.37(3H, s), 7.74(1H, dd, J=1, 8 Hz), 7.86(1H, t, J=8 Hz), 8.28(1H, dd, J=1, 8 Hz), 8.85(1H, s).

Example 54

3-(Piperidin-1-yl)sulfonyl-1-dimethylcarbamoyl-1H-1,2,4-triazole

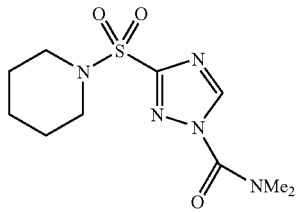

lp;-2p a) 3-Chlorosulfonyl-1-dimethylcarbamoyl-1H-1,2,4-triazole

A mixture of 3-benzylthio-1-dimethylcarbamoyl-1H-1,2,4-triazole (Example 1) (45 g), acetic acid (300 ml) and water (75 ml) was cooled below −5° C. on an ice-sodium chloride bath, and chlorine gas was passed into the mixture for 55 minutes. Water (600 ml) was added to the reaction solution, which in turn was extracted with ethyl acetate/hexane (1/1). The organic layer was washed with water, followed by an aqueous sodium hydrogencarbonate solution and then saturated aqueous sodium chloride solution, dried over anhydrous magnesium sulfate, and concentrated under reduced pressure to yield the title compound (33 g).

$^1$H-NMR(CDCl$_3$) δ=3.23(3H, br.s), 3.37(3H, br.s), 8.96 (1H, s).

b) 3-(Piperidin-1-yl)sulfonyl-1-dimethylcarbamoyl-1H-1,2,4-triazole

To a mixture of 3-chlorosulfonyl-1-dimethylcarbamoyl-1H-1,2,4-triazole (240 mg) and ethyl acetate (2 ml) was added pyridine (0.2 ml) on a water bath at room temperature. At this temperature the mixture was stirred for 1 hour. The reaction solution was washed with water, followed by saturated aqueous sodium chloride solution, and concentrated. The residue was subjected to a silica-gel column chromatography with 20 to 30% (20% 2-propanol/ethyl acetate)/hexane to yield the title compound (29 mg).

$^1$H-NMR(CDCl$_3$) δ=1.50–1.72(6H, m), 3.20(3H, br.s), 3.30–3.38(7H, m), 8.84(1H, s).

Example 55

3-(8-Azabicyclo[3.2.1]octan-8-yl)sulfonyl-1-dimethylcarbamoyl-1H-1,2,4-triazole

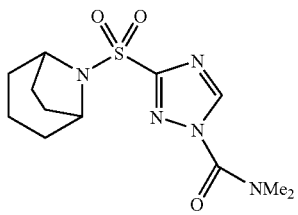

a) 8-Azabicyclo[3.2.1]octane hydrochloride

A mixture of tropane (900 mg), 1-chloroethyl chloroformate (1 ml), and toluene (20 ml) was heated and refluxed for 6 hours. After that, methanol (10 ml) was added to the reaction solution, and further refluxed for 4 hours. The solvent was distilled to yield the title compound (850 mg).

b) 3-(8-Azabicyclo[3.2.1]octan-8-yl)sulfonyl-1-dimethylcarbamoyl-1H-1,2,4-triazole A mixture of 3-chlorosulfonyl-1-dimethylcarbamoyl-1H-1,2,4-triazole (Example 54-a) (470 mg), 8-azabicyclo[3.2.1] octane hydrochloride (350 mg), triethylamine (0.7 ml), and ethyl acetate (10 ml) was stirred overnight at room temperature. The reaction solution was washed with water, followed by saturated aqueous sodium chloride solution, and concentrated. The residue was subjected to a silica-gel column chromatography with 50 to 100% ethyl acetate/hexane to yield the title compound (150 mg).

$^1$H-NMR(CDCl$_3$) δ=1.40–1.80(8H, m), 1.84–1.95(2H, m), 3.19(3H, br.s), 3.33(3H, br.s), 4.35–4.45(2H, m), 8.80 (1H, s)

Example 56

3-(3,5-Dimethylpyrazol-1-yl)sulfonyl-1-dimethylcarbamoyl-1H-1,2,4-triazole

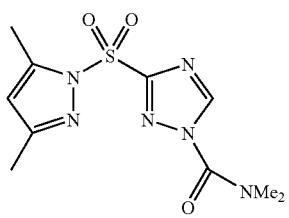

A mixture of 3,5-dimethylpyrazole (100 mg), 3-chlorosulfonyl-1-dimethylcarbamoyl-1H-1,2,4-triazole (Example 54-a) (480 mg), anhydrous potassium carbonate (280 mg), and acetonitrile (1.5 ml) was heated and stirred for 2 hours on an oil bath at 50° C. The reaction solution was extracted with ethyl acetate-water. The organic layer was washed with saturated aqueous sodium chloride solution, and concentrated. The residue was subjected to a silica-gel column chromatography with 20 to 30% (20% 2-propanol/ethyl acetate)/hexane, and the title compound (210 mg) was obtained by crystallization in ethyl acetate-hexane.

$^1$H-NMR(CDCl$_3$) δ=2.22(3H, s), 2.62(3H, s), 3.18(3H, s), 3.33(3H, s), 6.03(1H, s), 8.81(1H, s).

Example 57

3-(2,3-Dihydro-1H-indol-1-yl)sulfonyl-1-dimethylcarbamoyl-1H-1,2,4-triazole

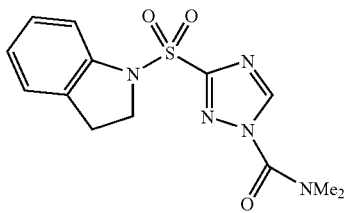

2,3-Dihydro-1H-indole was employed to synthesize the title compound as in Example 56.

$^1$H-NMR(CDCl$_3$) δ=3.12(2H, t, J=8 Hz), 3.14(6H, s), 4.26(2H, t, J=8 Hz), 7.00(1H, t, J=8 Hz), 7.10–7.17(2H, m), 7.53(1H, d, J=8 Hz), 8.75(1H, s).

Example 58

3-[N-(4-chlorophenyl)-N-methylamino]sulfonyl-1-dimethylcarbamoyl-1H-1,2,4-triazole

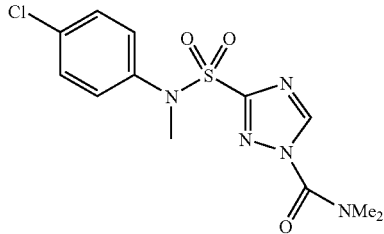

N-methyl-4-chloroaniline was employed to synthesize the title compound as in Example 56.

$^1$H-NMR(CDCl$_3$) δ=3.17(3H, br.s), 3.23(3H, br.s), 3.47 (3H, s), 7.25(2H, d, J=9 Hz), 7.30(2H, d, J=9 Hz), 8.86(1H, s).

Example 59

3-(4-Toluenesulfonyl)-1-dimethylcarbamoyl-1H-pyrazole

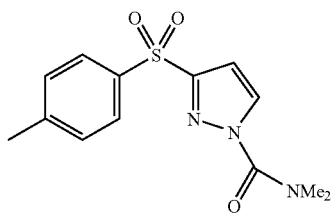

a) 1-(4-Toluenesulfonyl)-1H-pyrazole

A suspension of pyrazole (1 g) and 4-toluenesulfonyl chloride (2.8 g) in pyridine (10 ml) was stirred at 130° C. for 1 hour. After the reaction mixture was cooled, water was added to the reaction mixture, resulting in a white suspension. The resultant suspension was filtered, and the obtained white solids were washed three times with water. Drying at room temperature under reduced pressure gave white solids (500 mg).

$^1$H-NMR(d6-DMSO)δ=2.39(3H, s), 6.59–6.60 (1H, m), 7.47 (2H, d, J=8.2 Hz), 7.85–7.88 (3H, m), 8.46 (1H, d, J=2.8 Hz).

b) 3-(4-Toluenesulfonyl)-1-dimethylcarbamoyl-1H-pyrazole

Under a nitrogen atmosphere, a 1.6 M solution of tert-butyl lithium in hexane was added dropwise, at −70° C., to a solution of 1-(4-toluenesulfonyl)-1H-pyrazole (500 mg) in tetrahydrofuran (10 ml). The resulting yellow suspension was allowed to be warmed by itself to room temperature, and then stirred at 100° C. for 14 hours. After the reaction mixture was cooled, and a mixture obtained by dilution with saturated aqueous ammonium chloride solution was extracted twice with ethyl acetate. The combined organic layers were dried over magnesium sulfate, and concentrated under reduced pressure to give a brown oil as the residue. A suspension of the whole residue, dimethylcarbamoyl chloride (0.5 ml) and potassium carbonate (200 mg) in N,N-dimethylformamide was stirred at room temperature for 30 minutes. To the reaction mixture were added ethyl acetate and water, and extraction was carried out with ethyl acetate. The obtained organic layer was washed twice with water and once with saturated aqueous ammonium chloride solution, dried over magnesium sulfate. The residue was purified by a short-column chromatography (eluent: n-hexane/ethyl acetate=3/1) to yield a clear oil (122 mg).

$^1$H-NMR(CDCl$_3$) δ=2.42(3H, s), 3.10–3.25(6H, m), 6.81 (1H, d, J=2.8 Hz), 7.32(2H, d, J=8.2 Hz), 7.91(2H, d, J=8.4 Hz), 8.11 (1H, d, J=2.8 Hz).

Example 60

3-(4-Toluenesulfonyl)-1-dimethylcarbamoyl-1H-1,2,4-triazole

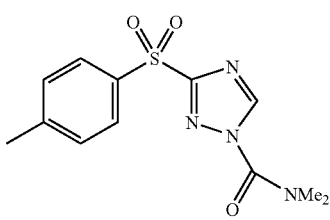

a) 1-(4-Toluenesulfonyl)-1H-triazole

To a solution of 1H-1,2,4-triazole (5 g) and 4-toluenesulfonyl chloride (14.5 g) in N,N-dimethylformamide was added sodium hydride (2.9 g) with cooling it on ice, and the reaction mixture was stirred for 40 minutes with cooling it on ice. To the reaction mixture was added water, and the resulting mixture was extracted with ethyl acetate. The obtained organic layer was washed twice with water, and then dried over magnesium sulfate. The residue was purified by a short-column chromatography (eluent: n-hexane/ethyl acetate=4/1) to yield white solids (21.8 g).

$^1$H-NMR (d6-DMSO) δ=2.42 (3H, s), 7.53 (2H, d, J=8.4 Hz), 7.97 (2H, d, J=8.4 Hz), 8.34(1H, s), 9.40 (1H, s).

b) 3-Toluenesulfonyl-1H-triazole

To a solution of 1-toluenesulfonyl-1-tetrazole (1 g) and lithium bromide (389 mg) in tetrahydrofuran was added dropwise a 2.6 M solution of butyl lithium in hexane at −78° C. The reaction mixture was stirred at −78° C. for 10 minutes, and then at room temperature for 3 hours and 30 minutes. Saturated aqueous ammonium chloride solution was added to the resulting reaction mixture with cooling it on ice, and the obtained mixture was extracted with ethyl acetate. The obtained organic layer was dried over magnesium sulfate. The solvent was distilled from the residue under reduced pressure, resulting in brown solids (440 mg).

$^1$H-NMR(d6-DMSO) δ=2.40 (3H, s), 7.47 (2H, d, J=7.8 Hz), 7.85 (2H, d, J=8.0 Hz), 8.80 (1H, s).

c) 3-(4-Toluenesulfonyl)-1-dimethylcarbamoyl-1H-1,2,4-triazole

A suspension of 3-(4-toluenesulfonyl)-1H-1,2,4-triazole (100 mg), dimethylcarbamoyl chloride (62 μl) and potassium carbonate (124 mg) in N,N-dimethylformamide was stirred at room temperature for 70 minutes. To the reaction mixture were added ethyl acetate and water, and extraction was carried out with ethyl acetate. The obtained organic layer was washed three times with water, and then dried over magnesium sulfate. The residue was purified by a short-column chromatography (eluent: n-hexane/ethyl acetate=3/1) to yield a clear oil (77 mg).

$^1$H-NMR (CDCl$_3$) δ=2.34(3H, s), 3.02(6H, br s), 7.48 (2H, d, J=8.0 Hz), 7.87(2H, d, J=8.0 Hz), 9.22(1H, s).

Test Example 1

Measurement of DPPIV Inhibiting Effects

DPP-IV, obtained from porcine kidneys, was dissolved in a reaction buffer solution (50 mM Tris-HCl, pH 7.4, 0.1% BSA) such that the concentration of DPP-IV was at 10 mU/mL. This solution (110 μl) was placed into test tubes, to which compounds to be tested were further added at a quantity of 15 μl and incubated at room temperature for 20 minutes. Twenty-five microliters of a solution in which Gly-Pro-p-nitroanilide was dissolved at 2 mM was added (final concentration, 0.33 mM) to start the enzymatic reaction. The reaction time was 20 minutes. The reaction was stopped by the addition of 25 μl of 1 N phosphoric acid. The absorbance at 405 nm was measured and the percent inhibition of the enzyme reaction was determined to calculate IC$_{50}$ values.

TABLE 1

| Example No. | IC$_{50}$(μM) | Example No. | IC$_{50}$(μM) |
|---|---|---|---|
| 1 | 4.69 | 2 | 1.39 |
| 3 | 0.784 | 4 | 0.657 |
| 5 | 1.346 | 6 | 3.462 |
| 7 | 0.192 | 8 | 3.363 |
| 9 | 0.219 | 10 | 0.694 |

TABLE 1-continued

| Example No. | IC$_{50}$(μM) | Example No. | IC$_{50}$(μM) |
|---|---|---|---|
| 11 | 0.216 | 12 | 1.73 |
| 13 | 0.164 | 14 | 2.22 |
| 15 | 0.311 | 16 | 5.53 |
| 17 | 0.416 | 18 | 4.53 |
| 19 | 0.233 | 20 | 1.370 |
| 21 | 0.688 | 22 | 2.29 |
| 23 | 1.94 | 24 | 0.0215 |
| 25 | 0.0574 | 26 | 0.244 |
| 27 | 0.0782 | 28 | 0.0584 |
| 29 | 0.00888 | 30 | 0.266 |
| 31 | 0.920 | 32 | 3.69 |
| 33 | 0.00951 | 34 | 6.63 |
| 35 | 1.51 | 36 | 0.000347 |
| 37 | 0.010 | 38 | 0.00163 |
| 39 | 0.0228 | 40 | 2.10 |
| 41 | 0.00425 | 42 | 0.551 |
| 43 | 0.00434 | 44 | 0.318 |
| 45 | 0.0324 | 46 | 1.77 |
| 47 | 0.103 | 48 | 1.55 |
| 49 | 0.0258 | 50 | 5.38 |
| 51 | 0.106 | 52 | 4.788 |
| 53 | 0.351 | 54 | 0.164 |
| 55 | 0.0961 | 56 | 0.101 |
| 57 | 0.230 | 58 | 0.0157 |
| 58 | 4.22 | 60 | 0.335 |

Test Example 2

Test for Identifying Glucose-Tolerance Improving Effects

Effects on Glucose-Tolerance Ability of Normal Mice

Animals: Five or six male C57BL/6N mice per group (purchased from Charles River Japan, Inc.).

Preparation and Administration of Compounds to be Tested:

Experiments 1 and 2

Compounds to be tested were suspended in a 0.5% aqueous solution of methylcellulose and mixed with an equal volume of a glucose solution, and administered orally at a volume of 10 ml/kg at doses indicated in Tables below. Vehicle control groups received orally a mixture of a 0.5% aqueous solution of methylcellulose and an equal volume of a glucose solution at a volume of 10 ml/kg. Glucose was given at a dose of 2 g/kg.

Experiment 3

A compound to be tested was suspended in a 0.5% aqueous solution of methylcellulose at a dose indicated in Table below. The suspension of the compound to be tested and 0.5% methylcellulose solution which was the vehicle control group were administered orally at a volume of 10 ml/kg, and at 30 minutes after administration, a glucose solution was administered orally at a volume of 10 ml/kg. Glucose was given at a dose of 2 g/kg.

Blood-Collecting and Measurement of Blood Glucose Values:

Experiments 1 and 2

The blood was drawn from the tail vein immediately before and at 30, 60, and 120 minutes after the administration of mixed solutions of the compounds to be tested and glucose, and subjected to the measurement of the blood glucose value.

Experiment 3

The blood was drawn from the tail vein immediately before the administration of the compound to be tested, and immediately before and at 30, 60, and 120 minutes after the administration of the glucose solution, and subjected to the measurement of the blood glucose value.

Methods:

The tail vein of the mice was injured, without anesthesia, with a razor to cause slight bleeding. Ten microliters of blood was collected, and mixed immediately with 14010 µl of 0.6 M perchloric acid. The glucose in supernatants obtained by centrifugation (1500 g, 10 min. 4° C., in a cooled centrifuge GS-6KR from Beckman Ltd.) was determined employing a Glucose CII Test Wako kit (Wako Pure Chemical Industries, Ltd.).

Results:

Results are shown in Table 2 below. The results are expressed by mean value±standard error.

TABLE 2

Effects on Glucose-Tolerance Ability of Normal Mice
Experiment 1:

| Tested Compound | Dose (mg/kg) | Blood Glucose (mg/dl), At Indicated Times (min.) After Oral Administration | | | |
|---|---|---|---|---|---|
| | | 0 | 30 | 60 | 120 |
| Vehicle Control | | 76.2 ± 3.0 | 218.6 ± 16.1 | 162.2 ± 10.3 | 113.2 ± 3.1 |
| Example 2 | 30 | 75.8 ± 1.5 | 159.8 ± 5.5 | 133.8 ± 4.1 | 109.6 ± 3.0 |

Experiment 2:

| Tested Compound | Dose (mg/kg) | Blood Glucose (mg/dl), At Indicated Times (min.) After Oral Administration | | | |
|---|---|---|---|---|---|
| | | 0 | 30 | 60 | 120 |
| Vehicle Control | | 74.5 ± 5.1 | 204.1 ± 11.4 | 157.5 ± 11.2 | 99.2 ± 3.5 |
| Example 13 | 3 | 73.9 ± 3.0 | 177.7 ± 6.3 | 139.7 ± 6.7 | 92.5 ± 2.4 |
| Example 13 | 10 | 73.3 ± 2.8 | 159.9 ± 9.9 | 129.3 ± 9.1 | 90.6 ± 3.2 |
| Example 13 | 30 | 70.4 ± 4.0 | 148.7 ± 5.1 | 127.3 ± 5.9 | 93.7 ± 2.3 |
| Example 13 | 100 | 72.0 ± 2.1 | 147.1 ± 16.2 | 133.7 ± 8.8 | 106.2 ± 5.4 |

Experiment 3:

| Tested Compound | Dose (mg/kg) | Blood Glucose (mg/dl), At Indicated Times After Glucose-Solution Administration (min.) | | | | |
|---|---|---|---|---|---|---|
| | | −30 | 0 | 30 | 60 | 120 |
| Vehicle Control | | 71.0 ± 3.1 | 81.2 ± 3.2 | 257.9 ± 12.1 | 246.7 ± 21.0 | 125.7 ± 9.1 |
| Ex. 43 | 1 | 70.8 ± 1.5 | 89.8 ± 2.1 | 173.8 ± 5.1 | 170.8 ± 5.7 | 112.1 ± 2.5 |

It is shown in the Tables that compounds of Examples 2, 13 and 43, in which N-carbamoylazole derivatives were used, provide a distinct effect on glucose-tolerance ability of normal mice through oral administration.

What is claimed is:

1. A method of treating diabetic diseases by using a dipeptidyl peptidase IV inhibiting agent represented by the general formula (I):

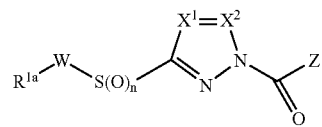

wherein $R^{1a}$ represents a $C_{1-6}$ alkyl group, a $C_{3-8}$ cycloalkyl group, a 5 to 10-member aromatic heterocyclic group, a $C_{6-10}$ aromatic hydrocarbon-cyclic group, a 4- to 10-member heterocyclic group, or a $C_{4-13}$ polycycloalkyl group;

n means an integer of 2;

W represents a single bond, or a $C_{1-6}$ alkylene group;

$X^1$ repesents a nitrogen atom, and $X^2$ represents a methine group;

Z represents a group represented by following formula Z-1:

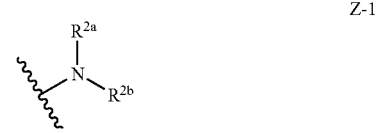

wherein each of $R^{2a}$ and $R^{2b}$ independently represents a $C_{1-6}$ alkyl group, or a $C_{2-6}$ alkenyl group; and wherein $R^{1a}$ may be substituted with one to three substituents selected from the group consisting of (1) halogen atoms, (2) a hydroxyl group, (3) $C_{2-6}$ alkenyl groups, (4) $C_{2-6}$ alkynyl groups, (5) a phenyl group, (6) a cyano group, (7) $C_{1-6}$ alkoxy groups which may be substituted with one to three halogen atoms or $C_{1-6}$ alkoxy groups, and (8) $C_{1-6}$ alkyl groups which may be substituted with one to three halogen atoms or $C_{1-6}$ alkoxy groups.
2. The method according to claim 1, wherein Z is a group represented by the following formula Z-3:
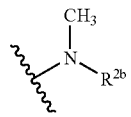
Z-3
wherein $R^{2b}$ represents a $C_{1-6}$ alkyl group, or a $C_{2-6}$ alkenyl group.
3. The method according to claim 1, wherein $R^{1a}$ is a phenyl group or a 4-pyrazolyl group.
* * * * *